United States Patent
Batcho et al.

(10) Patent No.: US 6,452,028 B1
(45) Date of Patent: *Sep. 17, 2002

(54) VITAMIN $D_3$ ANALOGS

(75) Inventors: Andrew David Batcho, North Caldwell; Bernard Michael Hennessy, Nutley; Jerome Anthony Iacobelli, Paramus; Milan Radoje Uskokovic, Upper Montclair, all of NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/648,825

(22) Filed: Aug. 25, 2000

Related U.S. Application Data

(62) Division of application No. 09/248,017, filed on Feb. 10, 1999, which is a division of application No. 09/163,037, filed on Sep. 29, 1998, now Pat. No. 5,939,408, which is a continuation of application No. 08/857,544, filed on May 16, 1997, now abandoned.

(60) Provisional application No. 60/018,153, filed on May 23, 1996, and provisional application No. 60/039,900, filed on Mar. 19, 1997.

(51) Int. Cl.[7] ............... C07C 401/00; A61K 31/593
(52) U.S. Cl. .................. 552/653; 514/167
(58) Field of Search ............... 552/653; 514/167, 514/168

(56) References Cited

U.S. PATENT DOCUMENTS

| | | | |
|---|---|---|---|
| 5,087,619 A | * | 2/1992 | Baggiolini et al. ......... 514/167 |
| 5,145,846 A | * | 9/1992 | Baggiolini et al. ......... 514/167 |
| 5,451,574 A | * | 9/1995 | Baggiolini et al. ......... 514/167 |
| 6,030,963 A | * | 2/2000 | Iacobelli et al. ............ 514/167 |

FOREIGN PATENT DOCUMENTS

| | | | |
|---|---|---|---|
| EP | 0325279 | * | 1/1989 |
| WO | 2000051554 | * | 8/2000 |

OTHER PUBLICATIONS

Uskokovic, Milan R. et al. (DN 128:488 Caplus, abstract of Gneral review, Vitam D (1997), 1045–1070, Editors: Feldman, D. et al., Academic: California).*

Uskokovic et al. DN 127:12746, Caplus, abstract of Curr. Pharm. Des. (1997), 3(1), 99–123).*

Rao, Leticia et al. (DN 134:217357, Caplus, abstract of Biological and Pharmaceutical Bullitin (2001), 24(3), 242–248).*

Nakagawa et al. (DN 134:232195, Caplus, abstract of Steroids 2001), 66(3–5), 327–337).*

T. Eguchi, et al., Chem. Pharm Bull. vol. 38, pp. 1246–1249.
A. Honda, et al., Steroids: Structure, Function & Regulation, vol. 56, No. 3, 3/91 pp. 142–146.

* cited by examiner

*Primary Examiner*—Sabiha Qazi
(74) *Attorney, Agent, or Firm*—George W. Johnston; Robert A. Silverman

(57) ABSTRACT

A compound of the formula

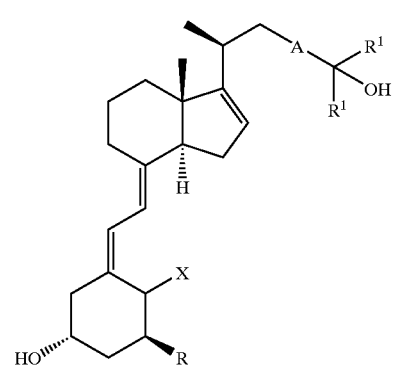

wherein R is hydrogen or hydroxy, each $R^1$ is ethyl, propyl, butyl, isopropyl or t-butyl, X is $=CH_2$, or when R is hydroxy, X is hydrogen or $=CH_2$, and A is —C≡C—,

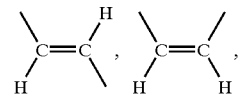

or

—$CH_2$—$CH_2$—.

These compounds are useful for the treatment of hyperproliferative disorders, skin diseases, and sebaceous gland diseases.

9 Claims, No Drawings

VITAMIN D₃ ANALOGS

This is a divisional application of Ser. No. 09/248,017, filed Feb. 10, 1999, which is a divisional of Ser. No. 09/163,037, filed Sep. 29, 1998 (U.S. Pat. No. 5,939,408), which is a continuation of Ser. No. 08/857,544, filed May 16, 1997 (now abandoned), which claims priority under 35 USC §119(e) of prior Provisional Application Ser. No. 60/018,153, filed May 23, 1996 and prior Provisional Application Ser. No. 60/039,900, filed Mar. 19, 1997.

BACKGROUND OF THE INVENTION

Field of the Invention

The invention relates to Vitamin D₃ analogs, particularly 20epi-16-ene analogs of Vitamin D₃.

SUMMARY OF THE INVENTION

The invention relates to compounds of the formula

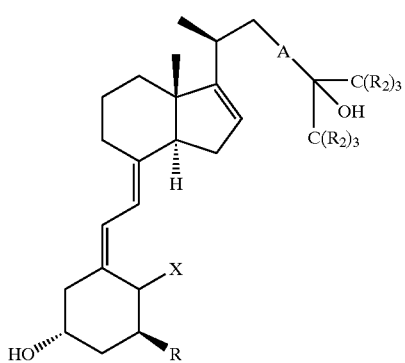

I wherein R is hydrogen, fluorine, or hydroxyl, R₂ is lower alkyl or C(R₃)₃ and R₃ is halogen, X is =CH₂ or when R is hydroxy, X is hydrogen or =CH₂, and A is —C≡C—,

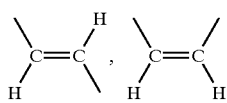

or
—CH₂—CH₂—, provided that when A is —CH₂—CH₂—, R₂ is lower alkyl.

Compounds of formula I induce differentiation and inhibition of proliferation in various skin and cancer cell lines. Accordingly, the compounds of formula I are useful as agents for the treatment of hyperproliferative skin diseases, such as, psoriasis. Compounds of formula I are also useful in the treatment of neoplastic diseases, such as, leukemia or breast cancer and sebaceous gland diseases, such as, acne or seborrheic dermatitis.

DETAILED DESCRIPTION OF THE INVENTION

As used herein, "lower alkyl" denotes a straight or branched chain alkyl group containing 1 to 4 carbon atoms, for example, methyl, ethyl, propyl, isopropyl, butyl, t-butyl and the like. Preferably lower alkyl is methyl or ethyl. Halogen means fluorine, iodine, bromine or chlorine, preferably, fluorine.

In the formulas presented herein, the various substituents are illustrated as joined to the nucleus by one of the following notations: a wedged solid line (◢) indicating a substituent which is above the plane of the molecule (β-orientation) and a wedged dotted line (⋯⫼) indicating a substituent which is below the plane of the molecule (α-orientation).

As used herein, the term "E" denotes

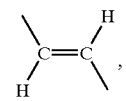

that is, a stereochemical configuration about a carbon-carbon double bond, such that the two hydrogens are attached to different carbon atoms, and are on opposite sides of the carbon-carbon double bond.

The term "Z" denotes

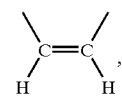

that is a stereochemical configuration about a carbon-carbon double bond, such that the two hydrogens are attached to different carbon atoms and are on the same side of the carbon-carbon double bond.

The invention relates to compounds of the formula

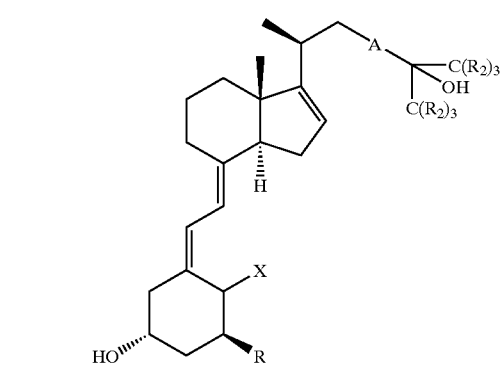

I wherein R is hydrogen, fluorine, or hydroxyl, R₂ is lower alkyl or C(R₃)₃ and R₃ is halogen, X is =CH₂, or when R is hydroxy X is hydrogen or =CH₂, and A is —C≡C—,

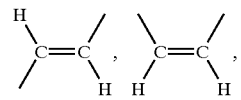

or
—CH₂—CH₂—, provided that when A is —CH₂—CH₂—, R₂ is lower alkyl.

Compounds of formula I induce differentiation and inhibition of proliferation in various skin and cancer cell lines. Accordingly, the compounds of formula I are useful as agents for the treatment of hyperproliferative skin diseases, such as, psoriasis. Compounds of formula I are also useful in the treatment of neoplastic diseases, such as, leukemia or breast cancer and sebaceous gland diseases, such as, acne or seborrheic dermatitis. Compounds of formula I, particularly 1α-fluoro-25-hydroxy-16,23E-diene-26,27-bishomo-20-epi-chole-calciferol, are useful in the treatment of osteoporosis, see U.S. copending patent application Ser. No. 08/857,569, filed May 16, 1997, which is incorporated by reference herein.

The invention also relates to a pharmaceutical composition comprising a compound of formula I and a method of treating neoplastic diseases, sebaceous gland diseases and hyperproliferative skin diseases by administration of a compound of formula I.

The invention also relates to a process for preparing compounds of formula I and intermediates of formula XII.

In a preferred embodiment, R is hydroxyl. In a compound of formula I, $R_2$ is preferably hydrogen or fluorine. In a preferred compound of formula I, A is double bond or triple bond or single bond. Preferred compounds of formula I are:

1,25-dihydroxy-16-ene-23-yne-20-epi-cholecalciferol;
1,25-dihydroxy-16-ene-20-epi-cholecalciferol;
1,25-dihydroxy-16-ene-23-yne-26,27-hexafluoro-20-epi-cholecalciferol;
1α-fluoro-25-hydroxy-16,23Z-diene-26,27-hexafluoro20-epi-cholecalciferol;
1α-fluoro-25-hydroxy-16-ene-23-yne-26,27-hexafluoro20-epi-cholecalciferol;
1,25-dihydroxy-16,23E-diene-26,27-hexafluoro-20-epi-cholecalciferol;
1,25-dihydroxy-16,23Z-diene-26,27-hexafluoro-20-epi-cholecalciferol;
1,25-dihydroxy-16,23Z-diene-19-nor-26,27-hexafluoro-20epi-cholecalciferol.

The compounds of formula I are prepared as hereafter described in Schemes I–V and the Examples.

SCHEME I

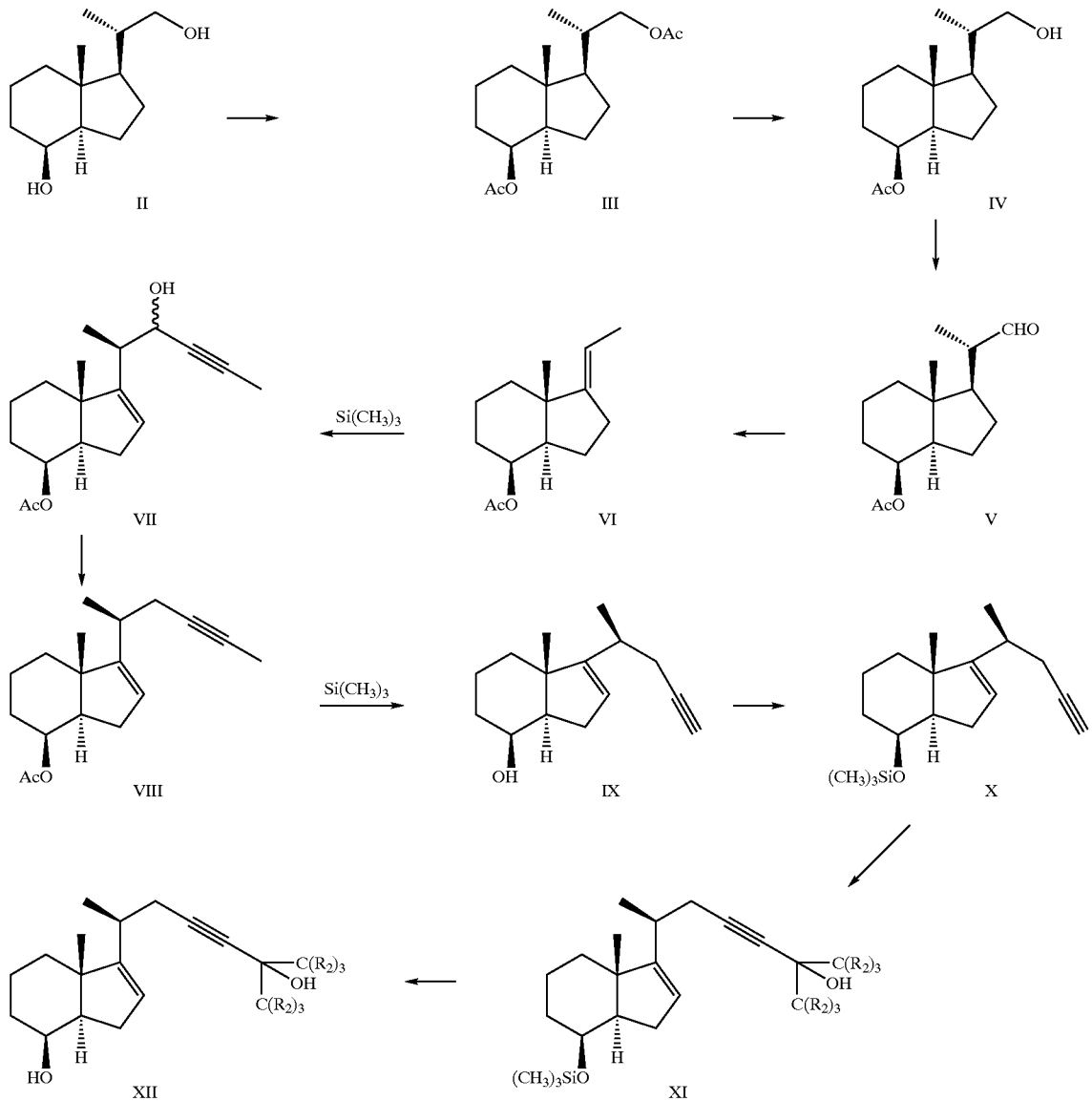

wherein $R_2$ is as described above.

In above Scheme I, the compound of formula II, a known compound (B. M. Trost, P. R. Bernstein, P. C. Funfschilling, J. American Chemical Society 101, 4378 (1979)), is converted to the compound of formula III by reaction with acetic anhydride, pyridine and dimethylaminopyridine in a chlorinated hydrocarbon solvent, such as dichloromethane. The reaction is carried out at 0° C. to 50° C., preferably room temperature, preferably under an argon atmosphere.

The compound of formula III is converted to the compound of formula IV by reaction with a base, such as, sodium carbonate in an alcohol solvent, such as methanol, under, preferably, an argon atmosphere.

The compound of formula IV is converted to the compound of formula V by reaction with oxalyl chloride and dimethylsulfoxide in a chlorinated hydrocarbon solvent, such as, dichloromethane, under an argon atmosphere.

The compound of formula V is converted to the compound of formula VI by reaction with benzalacetone in the presence of palladium on charcoal catalyst.

The compound of formula VI is converted to the compound of formula VII by reaction with a 3-trimethylsilylpropynal and a Lewis acid such as dimethylaluminum chloride in a chlorinated hydrocarbon solvent, such as dichloromethane.

The compound of formula VII is converted to the compound of formula VIII by reaction of the corresponding phenylthiono-carbonate with tri-n-butylhydride and triethylborane in toluene.

The compound of formula VIII is converted to the compound of formula IX by reaction with a base, such as, sodium hydroxide in an alcohol solvent, such as ethanol. The reaction is carried out at a temperature in the range of 50° C. to 100° C., preferably 80° C.

The compound of formula IX is converted to the compound of formula X by reaction with 1-(trimethylsilyl) imidazole in a chlorinated hydrocarbon solvent, such as anhydrous methylene chloride.

The compound of formula X is converted to a compound of formula XI by reaction with the corresponding compound of formula

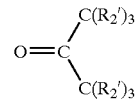

wherein $R_2'$ is hydrogen, or lower alkyl in the presence of a base such as n-butyllithium.

The reaction is preferably carried out at −78° C.

When the compounds of formula I wherein $R_2$ is halogen are prepared, the compound of formula X is reacted with a halogenated acetone, such as hexafluoroacetone in the presence of a base such as n-butyllithium.

The compound of formula XI is converted to the corresponding compound of formula XII by reaction with tetrabutylammonium fluoride in an ether solvent such as, tetrahydrofuran.

SCHEME II

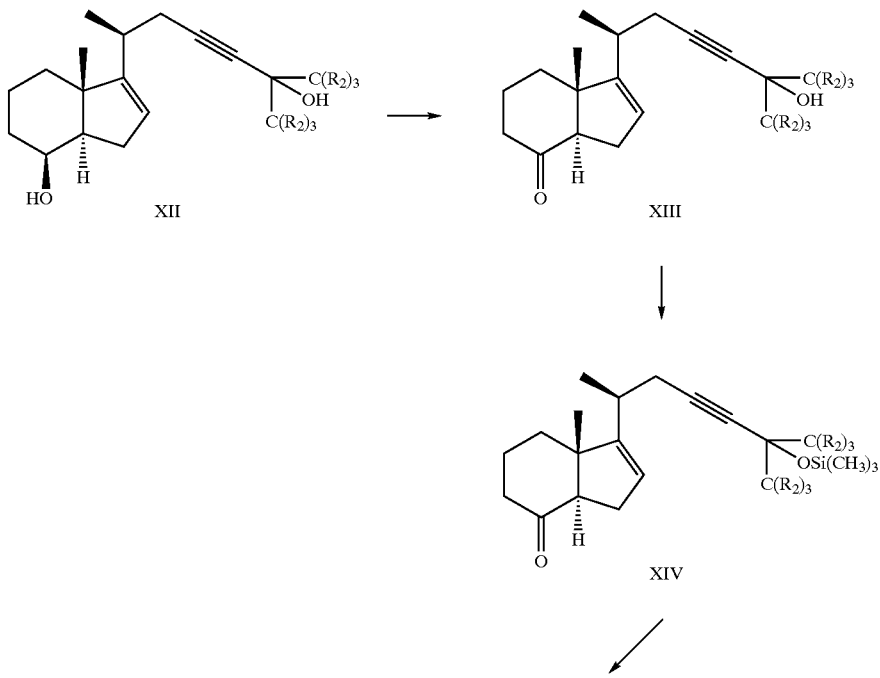

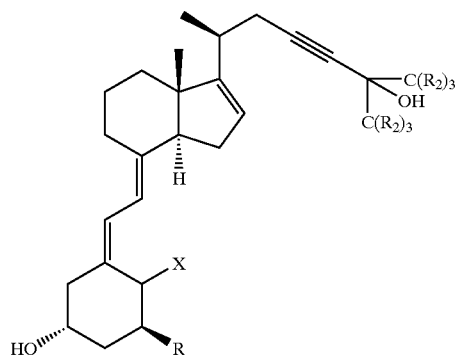

Ia wherein R, X and $R_2$ are as described above.

As set forth in Scheme II, a compound of formula XII is converted to a corresponding compound of formula XIII by reaction with an oxidizing agent such as, pyridinium dichromate in a chlorinated hydrocarbon solvent such as, anhydrous methylene chloride.

A compound of formula XIII is converted to a corresponding compound of formula XIV by reaction with 1-(trimethylsilyl)imidazole in a chlorinated hydrocarbon solvent, such as, anhydrous methylene chloride.

A compound of formula XIV is converted to a corresponding compound of formula Ia wherein R is hydroxy and X is =CH$_2$, by reaction with [3S-(1Z,3α,5β)]-[2-[3,5-bis[[1,1-dimethylethyl)-dimethylsilyl]oxy]-2-methylene-cyclohexylidene]ethyl]diphenyl-phosphine oxide in an ether like solvent such as tetrahydrofuran in the presence of n-butyllithium as a base.

Alternatively, a compound of formula XIV is converted to the corresponding compound of formula Ia wherein R is hydrogen by reaction with [5S,Z]-2-[2-[2-methylene-5-[[(1,1-dimethylethyl)-dimethylsilyl]oxy]cyclohexylidene]ethyl]diphenylphosphine oxide in an ether like solvent such as tetrahydrofuran in the presence of n-butyllithium as a base.

Alternatively, a compound of formula XIV is converted to the corresponding compound of formula Ia wherein R is fluorine by reaction with [3S-(3α,5β,Z)]-2-[2-[2-methylene-3-fluoro-5-[[( 1,1-dimethylethyl)dimethylsilyl]oxy] cyclohexylidene]ethyl]diphenyl-phosphine oxide in a ether like solvent such as tetrahydrofuran in the presence of n-butyllithium as a base.

Alternatively, a compound of formula XIV is converted to the corresponding compound of formula Ia wherein R is hydroxy and X is hydrogen by reaction with [3R-(3α,5β,Z)-3,5-bis[[(1,1-dimethylethyl)-dimethylsilyl]oxyl] cyclohexylidene]ethyl]diphenylphosphine oxide in an ether like solvent, such as tetrahydrofuran in the presence of nbutyllithium as a base.

SCHEME III

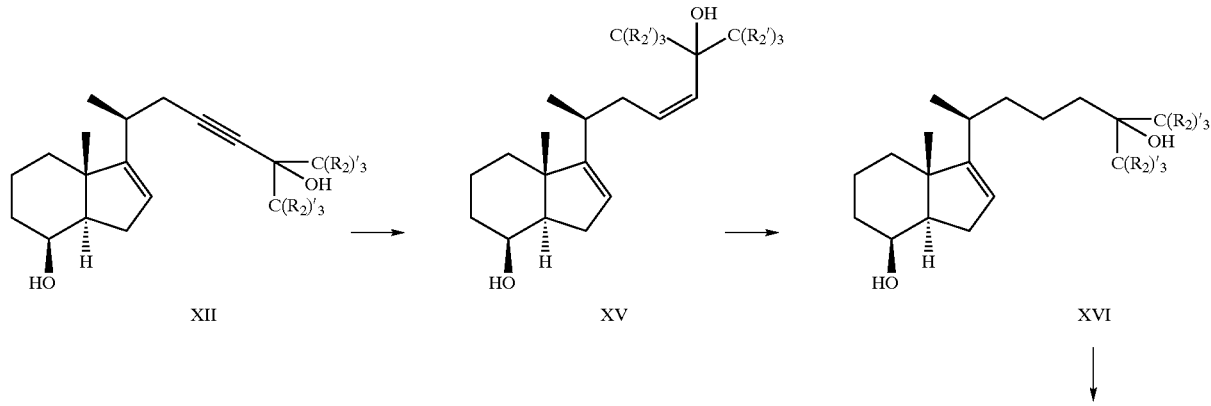

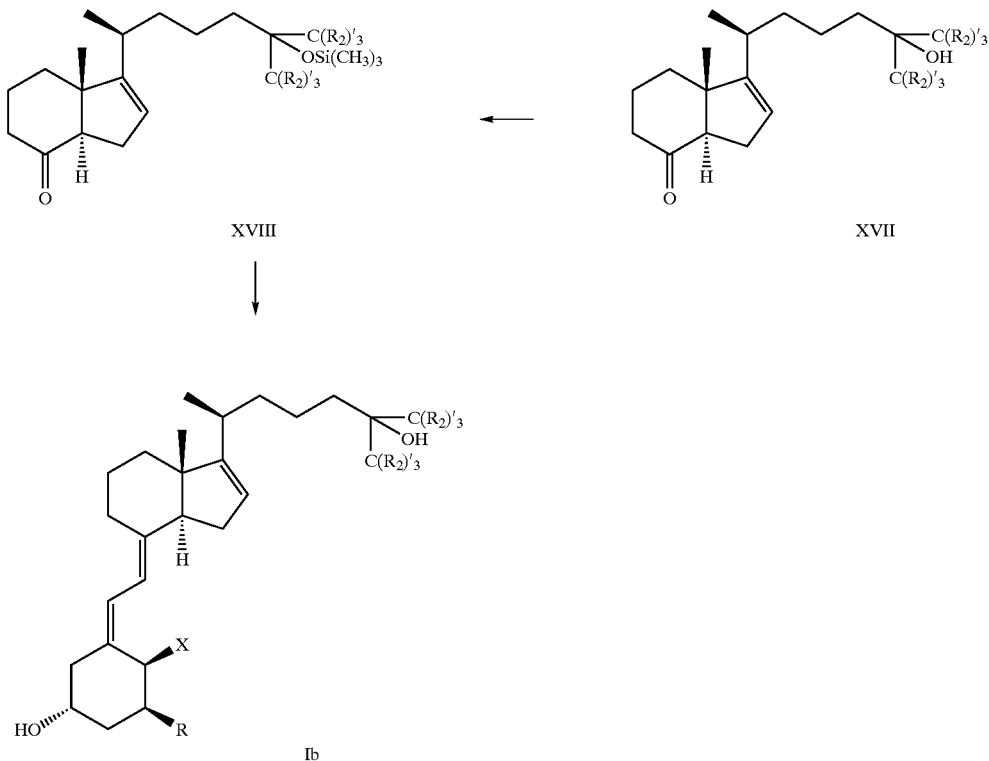

wherein R, X are as described above and $R_2'$ is hydrogen or lower alkyl.

In the above Scheme III, a compound of formula XII is reduced to a corresponding compound of formula XV by reaction with hydrogen and Lindlar catalyst in an organic solvent, such as, a combination of ethyl acetate, hexane and ethanol, in the presence of quinoline.

A compound of formula XV is converted to a corresponding compound of formula XVI by reaction with hydrogen in the presence of a catalyst such as 1,4-bis (diphenylphosphino)butane 1,5-cyclooctadiene rhodium tetrafluoroborate and mercury in a chlorinated hydrocarbon solvent, such as, methylene chloride.

A compound of formula XVI is oxidized to a corresponding compound of formula XVII by reaction with pyridinium dichromate in a chlorinated hydrocarbon solvent, such as methylene chloride.

A compound of formula XVII is converted to a corresponding compound of formula XVIII by reaction with 1-(trimethylsilyl)-imidazole in a chlorinated hydrocarbon solvent, such as methylene chloride.

A compound of formula XVIII is converted to a corresponding compound of formula Ib wherein R is hydroxy and X is =$CH_2$, by reaction with [3S-(1Z,3α,5β)]-[2-[3,5-bis[[1,1-dimethylethyl)-dimethylsilyl]oxy)-2-methylene-cyclohexylidene]ethyl]diphenyl phosphine oxide in the presence of n-butyllithium as a base, preferably at a temperature of –78° C. in anhydrous tetrahydrofuran as solvent.

Alternatively, a compound of formula XVIII is converted to a corresponding compound of formula Ib wherein R is hydroxy and X is hydrogen by reaction with [3R-(3α,5β, Z)-3,5-bis[[(1,1-dimethylethyl)dimethylsilyl]oxy] cyclohexylidene]ethyl]diphenylphosphine oxide in the presence of n-butyllithium as a base in anhydrous tetrahydrofuran as a solvent.

Alternatively, a compound of formula XVIII is converted to the corresponding compound of formula Ib wherein R is fluorine by reaction with [3S-(3α,5β,Z)]-2-[2-[2-[methylene-3-fluoro-5-[[1,1 dimethylethyl)dimethylsilyl] oxy]cyclohexylidene]ethyl]diphenylphosphine oxide in the presence of n-butyllithium as a base in anhydrous tetrahydrofuran as a solvent, at a temperature of –78° C.

Alternatively, a compound of formula XVIII is converted to the corresponding compound of formula Ib wherein R is hydrogen by reaction with [5S,Z]-2-[2-[2-methylene-5-[[1, 1-dimethylethyl)dimethylsilyl]oxy]cyclohexylidene]ethyl] diphenylphosphine oxide in the presence of n-butyllithium as a base in anhydrous tetrahydro-furan as a solvent at a temperature of –78° C.

SCHEME IV

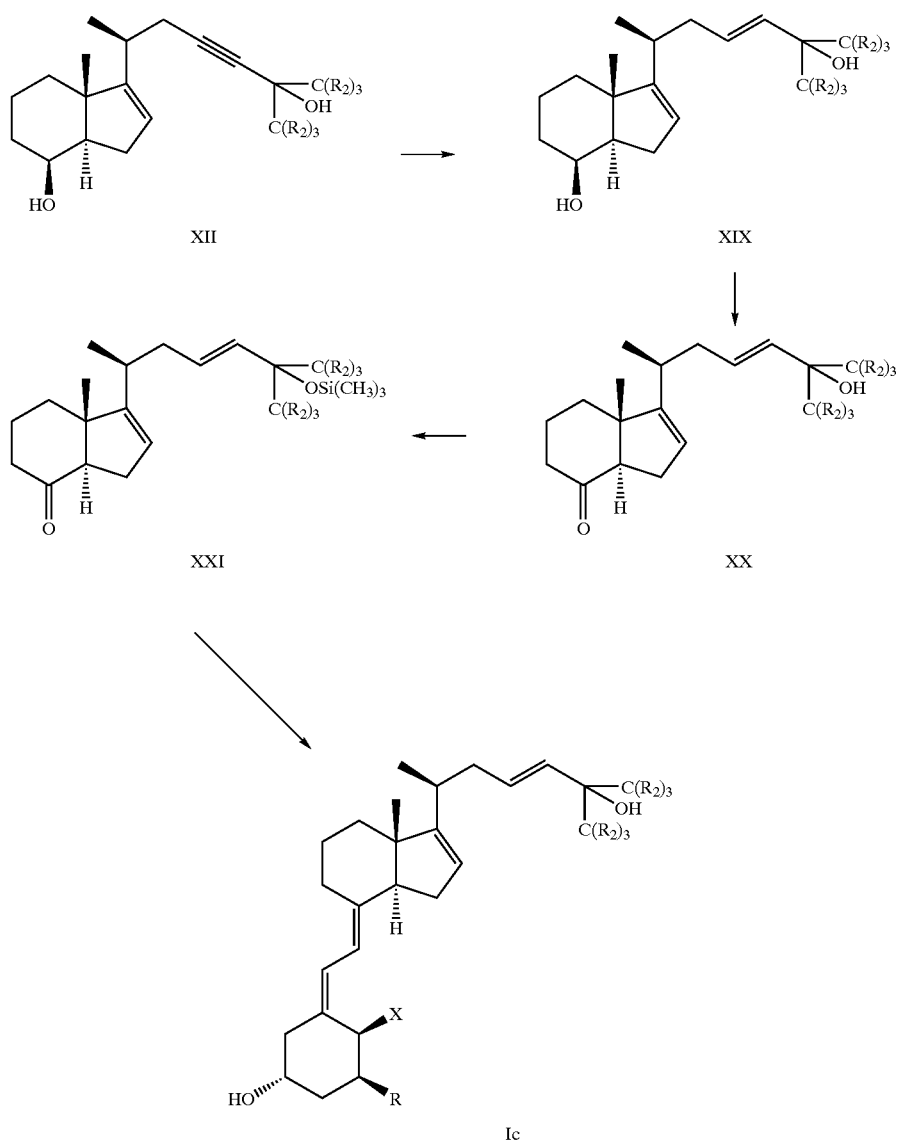

wherein R, X and $R_2$ are as described above.

In above Scheme IV, a compound of formula XII is converted to a corresponding compound of formula XIX by reaction with a reducing agent such as, lithium aluminum hydride in an ether solvent, such as, tetrahydrofuran in the presence of sodium methoxide as a base.

A compound of formula XIX is converted to a corresponding compound of formula XX by reaction with an oxidizing agent such as, pyridinium dichromate in a chlorinated hydrocarbon solvent, such as, methylene chloride.

A compound of formula XX is converted to a corresponding compound of formula XXI by reaction with 1-(trimethylsilyl)-imidazole in a chlorinated hydrocarbon solvent, such as, methylene chloride.

A compound of formula XXI is converted to a corresponding compound of formula Ic wherein R is hydroxy and X is =CH$_2$, by reaction with [3S-(1Z,3α,5β)]-[2-[3,5-bis[[1,1-dimethylethyl)-dimethylsilyl]oxy]-2-methylene-cyclohexylidene]ethyl]diphenyl-phosphine oxide in an ether solvent, such as, tetrahydrofuran, in the presence of a base, such as n-butyllithium.

Alternatively, a compound of formula XXI is converted to a corresponding compound of formula Ic wherein R is hydroxy and X is hydrogen by reaction with [3R-(3α,5β,Z)]-3,5-bis[[1,1-dimethyl-ethyl)-dimethylsilyl]oxy]cyclohexylidene]ethyl]diphenylphosphine oxide in an ether solvent, such as tetrahydrofuran, in the presence of a base, such as n-butyllithium.

Alternatively, a compound of formula XXI is converted to a corresponding compound of formula Ic wherein R is hydrogen by reaction with [5S,Z]-2-[2-[2-methylene-5-[[1,1-dimethylethyl)-dimethylsilyl]oxy]cyclohexylidene]ethyl]diphenylphosphine oxide in an ether like solvent such as, tetrahydrofuran, in the presence of a base such as n-butyllithium.

Alternatively, a compound of formula XXI is converted to a corresponding compound of formula Ic wherein R is fluorine by reaction with [3S-(3α,5β,Z)]-2-[2-[2-methylene-3-fluoro-5-[[(1,1dimethylethyl)dimethylsilyl]oxy]cyclohexylidene]ethyl]diphenylphosphine oxide in a ether like solvent, such as tetrahydrofuran, in the presence of a base such as n-butyllithium.

SCHEME V

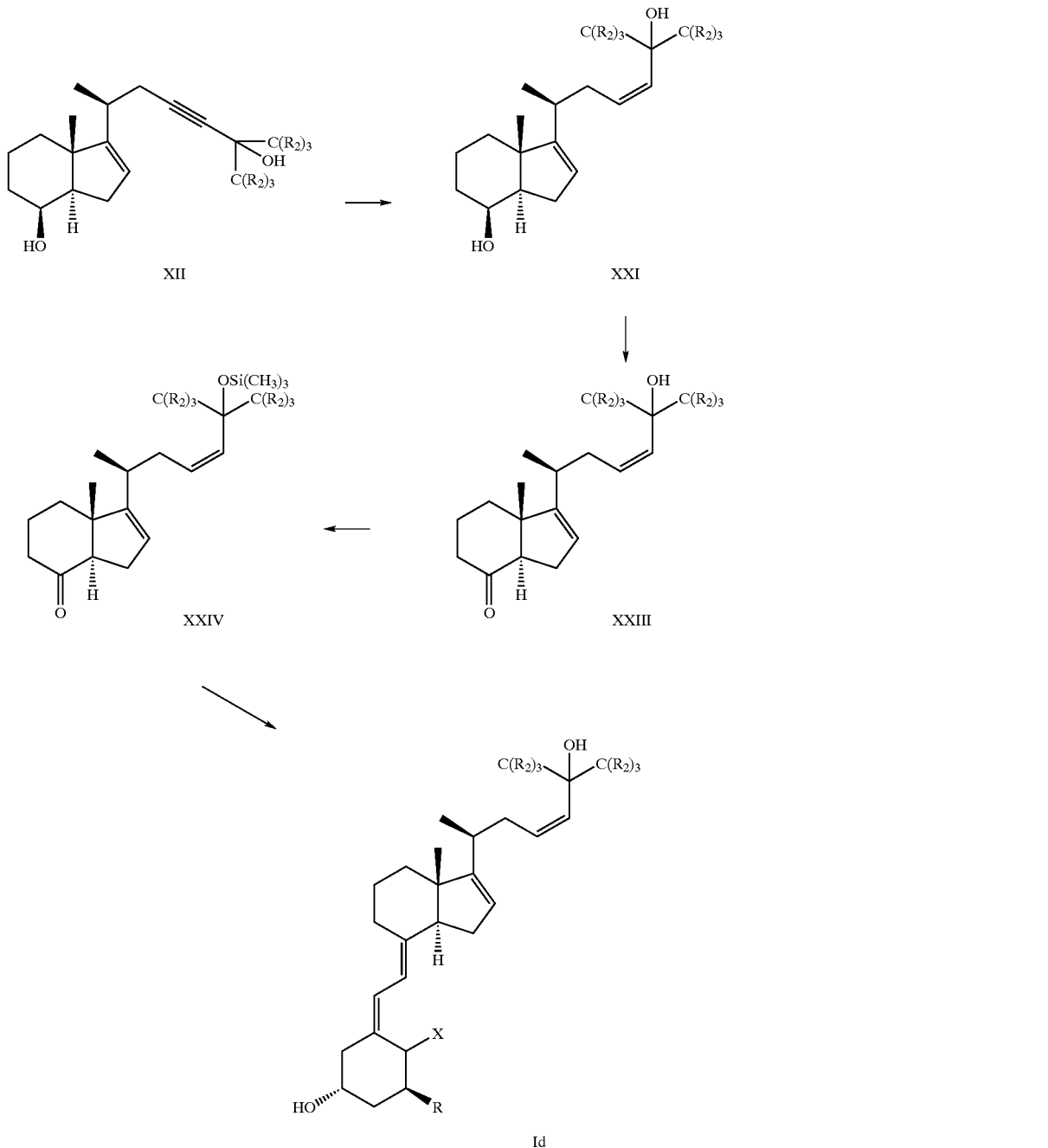

wherein R, X and $R_2$ are as described above.

As set forth in Scheme V above, a compound of formula XII is converted to a corresponding compound of formula XXII by hydrogenation with Lindlar catalyst in the presence of quinoline in a mixture of solvents, such as a combination of ethyl acetate, hexane and ethanol.

A compound of formula XXII is converted to a corresponding compound of formula XXIII by reaction with oxidizing agent, such as, pyridinium dichromate in a chlorinated hydrocarbon solvent, such as, methylene chloride.

A compound of formula XXIII is converted to a corresponding compound of formula XXIV by reaction with 1-(trimethylsilyl)imidazole in a chlorinated hydrocarbon solvent, such as, methylene chloride.

A compound of formula XXIV is converted to the corresponding compound of formula Id wherein R is hydroxy and X is $CH_2$, by reaction with [3S-(1Z ,3α,5β)]-[2-[3,5-bis [[1,1-dimethylethyl)dimethylsilyl]oxy]-2-methylenecyclohexylidene]ethyl]diphenylphosphine oxide in an ether solvent, such as tetrahydrofuran, in the presence of a base such as butyl lithium.

Alternatively, a compound of formula XXIV is converted to the corresponding compound of formula Id wherein R is hydroxy and X is hydrogen by reaction with [3R-(3α,5β, Z)]-3,5-bis [[(1,1-dimethyl-ethyl)dimethylsilyl]oxy]

cyclohexylidene]ethyl]diphenylphosphine oxide in tetrahydrofuran in the presence of a base such as n-butyllithium.

Alternatively, a compound of formula XXIV is converted to the corresponding compound of formula Id wherein R is hydrogen by reaction with [5S,Z]-2-[2-[2-methylene-5-[[(1,1-dimethylethyl)dimethylsilyl]oxy]cyclohexylidene]ethyl] diphenylphosphine oxide in an ether like solvent such as tetrahydrofuran in the presence of a base such as n-butyllithium.

Alternatively, a compound of formula XXIV is converted to the corresponding compound of formula Id wherein R is fluorine by reaction with [3S-(3α,5β,Z)]-2-[2-[2-methylene-3-fluoro-5-[[(1,1-dimethylethyl)dimethylsilyl]oxy] cyclohexylidene]ethyl]diphenylphosphine oxide in an ether like solvent such as tetrahydrofuran in the presence of a base such as n-butyllithium.

The compounds of formula I can be administered orally, for example, in the form of tablets, coated tablets, dragees, hard or soft gelatin capsules, solutions, emulsions or suspensions. The administration can, however, also be effected rectally, for example, in the form of suppositories or parenterally, for example, in the form of injection solutions.

A composition in accordance with the invention can be processed with pharmaceutically inert, inorganic or organic excipients for the manufacture of tablets, coated tablets, dragees and hard gelatin capsules. Lactose, corn starch or derivatives thereof, talc, stearic acid or its salts, and the like, can be used as such excipients, for example, for tablets, dragees and hard gelatin capsules.

Suitable excipients for soft gelatin capsules are, for example, vegetable oils, waxes, fats, semi-solid and liquid polyols, and the like; depending on the nature of the active ingredient. No excipients are, however, usually required in the case of soft gelatin capsules.

Suitable excipients for the preparation of solutions and syrups, are, for example, water, polyols, saccharose, invert sugar, glucose and the like.

Suitable excipients for injection solutions are, for example, water, alcohols, polyols, glycerol, vegetable oils, and the like.

Suitable excipients for suppositories are, for example, natural or hardened oils, waxes, fats, semi-liquid or liquid polyols and the like.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants.

The compounds of formula I as described above can be administered orally or by injection, for the treatment of neoplastic diseases such as leukemia, to warmblooded animals which need such treatment. More specifically, the compounds of formula I as described above can be administered orally to an adult human in dosages that are in the range of about 0.25 to 50 μg per day for the treatment of neoplastic diseases such as leukemia or breast cancer.

The compounds of formula I as described above can be administered orally, for the treatment of hyperproliferative skin diseases such as psoriasis, basal cell carcinomas, disorders of keratinization, and keratosis, to warmblooded animals which need such treatment. More specifically, the compounds of formula I as described above can be administered orally to an adult human in dosages that are in the range of about 0.25 to 50 μg per day for the treatment of hyperproliferative skin diseases such as psoriasis, basal cell carcinomas, disorders of keratinization, and keratosis. These compounds can be administered orally for the treatment of acne in humans at a dosage of about 0.25 to 50 μg per day; preferably 0.5 to 5 μg per day.

The compounds of formula I as described above can be administered topically, for the treatment of hyperproliferative skin diseases such as psoriasis, basal cell carcinomas, disorders of keratinization, and keratosis, to warmblooded animals which need such treatment. More specifically, the compounds of formula I as described above can be administered topically in dosages that are in the range of about 0.5 to about 100 μg per gram of topical formulation per day, for the treatment of hyperproliferative skin diseases such as psoriasis, basal cell carcinomas, disorders of keratinization, and keratosis.

The compounds of formula I as described above can also be administered topically for the treatment of sebaceous gland diseases such as acne or seborrheic dermatitis.

The useful activity of compounds of formula I as agents for the treatment of neoplastic diseases can be demonstrated by the following test procedures.

HL-60 Cell Differentiation

The induction of differentiation of HL-60 cells was assayed by measuring their oxidative burst potential via the reduction of nitrobluetetrazolium (NBT).

HL-60 cells were maintained in RPMI 1640 medium supplemented with 10% fetal calf serum (FCS), 2 mM L-glutamine, 1 mM sodium pyruvate, 1% non-essential amino acids, 50 U/ml penicillin and 50 μg/ml streptomycin (RPMI/FCS). HL-60 cells (30,000 cells/90 μl of RPMI/ supplemented medium) were seeded into flat-bottomed microtiter wells. Immediately after seeding, 10 μl of test compounds diluted in supplemented RPMI medium were added to the wells at the same time to yield final concentrations between $10^{-11}$ and $10^{-6}$ M (starting from stock solutions of $10^{-2}$ M in ethanol stored at −20° C. and protected from light). After 3 days, the medium was removed from the wells with a multichannel pipette and replaced with 100 μl of NBT solution (1 mg/ml in phosphate buffered saline (PBS) with 200 nM phorbol myristate acetate (PMA). Following an additional hour incubation at 37° C. the NBT solution was removed and 100 μl of 10% sodium dodecyl sulfate (SDS) in 0.01 N HCl was added. The amount of the reduced NBT was quantified photometrically at 540 nm using an automated plate reader. The mean of 3 wells was calculated. S.E.M. were between 5 and 10%. Values were expressed as percent of maximal differentiation achieved with 100–1000 nM calcitriol in the same experiment. The concentration (nM) leading to 50% of this maximal value is determined graphically and given in Table I as $ED_{50}$.

TABLE I

| COMPOUND | $ED_{50}$ (nM) |
| --- | --- |
| 1,25-Dihydroxy-cholecalciferol | 6.0 |
| 1,25-Dihydroxy-16-ene-23-yne 26,27-hexafluoro-20-epi-chole-calciferol | 2.0 |
| 1,25-Dihydroxy-16,23E-diene-26,27-hexafluoro-20-epi-cholecalciferol | 0.37 |
| 1,25-Dihydroxy-16,23Z-diene-26,27-hexafluoro-20-epi-cholecalciferol | 2.3 |
| 1,25-Dihydroxy-16-ene-23-yne-20 epi-cholecalciferol | 15.0 |
| 1,25-Dihydroxy-16-ene-20-epi-cholecalciferol | 2.5 |
| 1α-Fluoro-25-hydroxy-16,23Z diene-26,27-hexafluoro-20-epi cholecalciferol | 20.0 |

TABLE I-continued

| COMPOUND | ED$_{50}$ (nM) |
|---|---|
| 1,25-Dihydroxy-16,23Z-diene-26,27-hexafluoro-20-epi-19-nor cholecalciferol | 4.5 |

Antiproliferative Activity in T47-D and MCF-7 Breast Carcinoma Cells

The two cell lines used in these experiments and their growth requirements are listed below:
1. T47-D breast carcinoma cells were grown in RPMI 1640 medium supplemented with 10 μg/ml bovine insulin, and 10% fetal bovine.
2. MCF-7 breast carcinoma cells were grown in MEM (Eagles) supplemented with non-essential amino acids, 1 mM sodium pyruvate, 10 μg/ml bovine insulin, and 10% fetal bovine serum.

Cells were grown in appropriate medium to late log phase (~80% confluency). T47-D or MCF-7 cells are then trypsinized and seeded at 4000 or 2000 cells/well, respectively. At 24 hour post seeding, serial dilution of ethanol-solubilized drugs are prepared in the same medium and added to triplicate wells at a final concentration of 1,000 to 0.1 nM and 0.1% ethanol. On day 3 to 7 post drug addition, 50 μl of a 5 mg/ml MTT solution (3-(4,5-dimethylthiazol-2-yl)-2,5- diphenyl tetrazolium bromide in phosphate-buffered saline) is added to each well and incubation is continued at 37° C. for 2.5 hours. The plates are then spun briefly by centrifugation at 800×g for 5 minutes, medium is aspirated from wells, and 50 μl ethanol/well is added to dissolve the formazan formed during the incubation period with MTT. After a 15 minute shaking, the optical density is determined for each well in an automatic plate reader at 570 and 660 nm. Percent inhibition of cell growth is calculated by comparing optical densities of cells treated with test compounds to those of cells treated only with 0.1% ethanol. IC$_{50}$ values are determined based on the Reed and Muench formula (Reed, L. J., and H. Muench, A simple method of estimating fifty percent endpoint. Am. J. Hyg. 27:493–497 (1938)) and the results are presented below in Table II.

TABLE II

| COMPOUND | T47-D | MCF-7 |
|---|---|---|
| 1,25-Dihydroxy-cholecalciferol | 81.0 | 149 |
| 1,25-Dihydroxy-16-ene-23-yne 26,27-hexafluoro-20-epi-cholecalciferol | 6.7 | 0.95 |
| 1,25-Dihydroxy-16,23E-diene-26,27-hexafluoro-20-epi-cholecalciferol | 10.0 | ND |
| 1α-Fluoro-25-hydroxy-16-ene-23-yne-26,27-hexafluoro-20-epi-cholecalciferol | | 11 |
| 1α-Fluoro-25-hydroxy-16,23E-diene-26,27-hexafluoro-20-epi-cholecalciferol | | 9 |
| 1,25-Dihydroxy-16-ene-23-yne-26,27-bishomo-20-epi-cholecalciferol | | 11 |
| 1,25-Dihydroxy-16-ene-23-yne-26,27-bishomo-19-nor-20-epi-cholecalciferol | | 12 |
| 1α-Fluoro-25-hydroxy-16,23E-diene-26,27-bishomo-20-epi-cholecalciferol | | 30 |

The useful activity of compounds of formula I as agents for the treatment of hyperproliferative skin disease can be demonstrated by the following.

Inhibition of Keratinocytes Proliferation

HaCaT cell line—The immortalized human cell line HaCaT was used. $^3$H-thymidine incorporation was measured in exponentially growing cultures after 6 days of culture in presence of the test compound.

Cell culture—HaCaT cells were cultured in Dulbecco's Modified Eagle Medium (DMEM) and Nutrient Mixture Ham's F12 (F12), 3:1 (v/v, ICN) containing 4.5 g/l glucose and supplemented with 10% fetal calf serum (Gibco, FCS), L-glutamine (Gibco, 2 mM), penicillin (Gibco, 50 UI/ml), streptomycin (Gibco, 50/μg/ml), EGF (10 ng/ml), hydrocortisone (400 ng/ml), cholera toxin (8.5 ng/ml) and insulin (5 ng/ml). The cells were maintained in a humidified atmosphere containing 5% $CO_2$ and 95% air and passaged every 3–4 days.

Inhibition of $^3$H-thymidine uptake —HaCaT cells (250 cells in complete culture medium) were seeded into 96-well culture dishes and incubated at 37° C. with 5% $CO_2$ and 95% air for 6 days. Inhibitors, dissolved at 10×concentration in 1% ethanol, were added immediately at the beginning of the assay. $^3$H-thymidine (5 Ci/mmol, Amersham) was added at a concentration of 1 μCi/well and cells were pulse-labeled for the last 6 hours of the growth period. Cells were then trypsinized for 10 minutes at 37° C. under a vigorous agitation and harvested on to a 96-well GF/C filter plate (Uni Filter, Packard) using a Micro Mate 196 cell harvester (Packard). After drying at 40° C. under vacuum for 20–30 minutes, 20 μl of Micro Scint 0 scintillator (Packard) were added and the radioactivity bound to the filters was counted on a TOP COUNT (Packard). The results are set forth in Table III.

TABLE III

| COMPOUND | IC$_{50}$ (nM) |
|---|---|
| 1,25-Dihydroxy-cholecalciferol | 55.0 |
| 1,25-Dihydroxy-16-ene-23-yne-26,27-hexafluoro-20-epi-cholecalciferol | 50.0 |
| 1,25-Dihydroxy-16,23E-diene-26,27-hexafluoro-20-epi-cholecalciferol | 0.7 |
| 1,25-Dihydroxy-16,23Z-diene-26,27-hexafluoro-20-epi-cholecalciferol | ND |
| 1,25-Dihydroxy-16-ene-23-yne-20-epi-cholecalciferol | 93.0 |
| 1,25-Dihydroxy-16-ene-20-epi-cholecalciferol | 4.0 |

The useful activity of compounds of formula I as agents for the treatment of sebaceous gland diseases can be demonstrated by the following.

Inhibition of Human Sebocyte Proliferation In Vitro

Sebaceous cells were isolated from adult human sebaceous glands by a combination of enzymatic and mechanical methods (Doran et al., Characterization Of Human Sebaceous Cells In Vitro, J. Invest. Dermatol. 96:341–8 (1991)). The cells were cultured in Iscove's medium containing 10% fetal calf serum and 4 μg/ml dexamethasone on a layer of growth-arrested 3T3 mouse fibroblasts. Cells were plated in medium without the test compound and then given test compound in fresh medium 24–48 hours after the initial plating. The cultures were given fresh medium, containing the test compound, every 48 hours. On the day of harvesting, the cultures were rinsed with 0.03% EDTA (ethylenediamine tetroacetic acid) in PBS (phosphate-buffered saline), to remove only the 3T3 fibroblasts, followed by incubation in 0.05% trypsin/0.03% EDTA. The cells were suspended, mixed vigorously to prepare a single cell suspension and counted in a hemocytometer. Stock solutions of compounds were made up as $10^{-2}$ M solutions in degassed 100% ethanol and stored at −20° C. in the dark. During experimental use, the solutions, which have been aliquoted, were brought to room temperature and used by diluting directly into complete medium to the appropriate concentration.

The compounds were tested for the inhibition of proliferation of sebaceous cell growth in vitro at $10^{-6}$, $10^{-7}$ and $10^{-8}$ M. The results are summarized in Table IV as the amount of compound necessary to inhibit the proliferation of sebaceous cells by 50% ($ED_{50}$) in nM as compared to a vehicle-treated culture.

TABLE IV

| COMPOUND | $ED_{50}$ (nM) |
|---|---|
| 1,25-Dihydroxycholecalciferol | 50 |
| 1,25-Dihydroxy-16-ene-23-yne 26,27-hexafluoro-20-epi-cholecalciferol | <10 |
| 1,25-Dihydroxy-16,23E-diene-26,27 hexafluoro-20-epi-cholecalciferol | <10 |
| 1,25-Dihydroxy-16,23Z-diene-26,27 hexafluoro-20-epi-cholecalciferol | ND |
| 1,25-Dihydroxy-16-ene-23-yne-20 epi-cholecalciferol | 50 |
| 1,25-Dihydroxy-16-ene-20-epi cholecalciferol | <1 |

Calcium Tolerance Test in Mice

Profound changes in calcium homeostasis strongly affect the weight development of mice.

Mice (25–30 g body weight) received daily subcutaneous administrations of the compound for 4 consecutive days. Body weight was registered just before and at the end of a 5 day treatment period. The "highest tolerated dose" (HTD) is the dose which results in zero weight gain during this treatment period. The results are set forth in Table V.

TABLE V

| COMPOUND | HTD ($\mu g/kg$) |
|---|---|
| 1,25-Dihydroxycholecalciferol | 0.5 |
| 1,25-Dihydroxy-16-ene-23-yne 26,27-hexafluoro-20-epi-cholecalciferol | 6.0 |
| 1,25-Dihydroxy-16,23E-diene-26,27 hexafluoro-20-epi-cholecalciferol | 2.5 |
| 1,25-Dihydroxy-16,23Z-diene-26,27 hexafluoro-20-epi-cholecalciferol | 2.5 |
| 1,25-Dihydroxy-16-ene-23-yne-20 epi-cholecalciferol | 100 |
| 1,25-Dihydroxy-16-ene-20-epi-cholecalciferol | 30 |
| 1α-Fluoro-25-hydroxy-16,23Z-diene-26,27-hexafluoro-20-epi-cholecalciferol | 8.0 |
| 1,25-Dihydroxy-16,23Z-diene-26,27-hexafluoro-20-epi-19-nor-cholecalciferol | 3.0 |

The following Examples are provided to further describe the invention and are not intended to limit it in any way.

EXAMPLE 1

1R-[1α(S*),3aα,4β,7aβ]]-4-(Acetyloxy)-octahydro-β,7a-dimethyl-1H-indene-1-ethanol acetate To a magnetically stirred solution of 14.06 g (25 mmole) of [1R-[1α(S*),3aα, 4β,7aβ]]-octahydro-4-hydroxy-β,7a-dimethyl-1H-indene-1-ethanol, a known compound, in 75 ml of dichloromethane under an argon atmosphere was added 47 ml. (33.8 g, 331 mmole) of acetic anhydride followed by 53.5 ml of pyridine and 1.0 g of dimethyl aminopyridine. After 3.5 hr, 25 ml of methanol was added. After 15 min., the reaction mixture was poured into 750 ml of 1 M phosphoric acid, and 400 ml of dichloromethane was added. The phases were separated and the aqueous phase was extracted 2 more times with 500 ml of dichloromethane. The organic phases were washed in a counter current manner with 250 ml of water followed by 750 ml of 1 M sodium bicarbonate to afford, after drying with $Na_2SO_4$ filtration, and evaporation, 19.85 g (quantitative yield) of [1R[1α(S*), 3aα,4β,7aβ]]-4-(acetyloxy)-octahydro-β,7a-dimethyl-1H indene-1-ethanol acetate as a white solid.

EXAMPLE 2

1R-[1α(S*),3aα,4β,7a, β]]4-(Acetyloxy)-octahydro-β,7a-dimethyl-1H-indene-1-ethanol To a magnetically stirred solution of 20.81 g (20.6 mmole) of [1R-[1α(S*),3aα,4β,7a,β]]-4-(acetyloxy)-octahydro-β, 7a-dimethyl-1H-indene-1-ethanol acetate in 200 ml of methanol under an argon atmosphere was added 8.18 g (77.2 mmole) of sodium carbonate. The suspension was stirred for 16 hr and then most of the methanol was removed under reduced pressure on a rotary evaporator. The concentrate was distributed between 300 ml of water and 250 ml of ether. The aqueous phase was extracted 3 more times with 250 ml of ether and the ether phases were washed in a counter current manner with 300 ml of water, dried with $Na_2SO_4$, filtered, and evaporated to give 18.02 g of crude product. Chromatography on medium pressure LC (Waters 500) gave, on elusion with 2:1 hexane-ethyl acetate, 1.42 g unhydrolyzed diacetate, 16.08 g (90% yield) of [1R-[1a(S*), 3aα,4β,7aβ]]-4-(acetyloxy)-octahydro-β,7a-dimethyl-1H-indene-1-ethanol as a colorless oil.

EXAMPLE 3

1R-[1α(S*),3aα,4β,7aβ]]-4-(Acetyloxy)-octahydro-α,7a-dimethyl-1-H-indene-1-acetaldehyde A two-liter three-neck flask fitted with magnetic stirring, thermometer, and dropping funnel and maintained under an argon atmosphere was charged with 6.62 ml (75.8 mmole) of oxalyl chloride in 50 ml of dichloromethane. The flask was cooled to −65° in a dry iceoacetone bath; then a solution of 10.7 ml (151 mmole) of dimethylsulfoxide in 125 ml of dichloromethane was added dropwise at a rapid rate over 20 min while maintaining the temperature at −62° to −63°. After the addition, the reaction was stirred for an additional 5 min.; then a solution of 16.0 g of [1R-[1α(S*),3aα,4β, 7aβ]-4-(acetyloxy)-octahydro-β,7a-dimethyl-1H-indene-1-ethanol in 200 ml of dichloromethane (dried over 4 Å molecular sieves) was added dropwise over 20 min. maintaining the temperature at −65°. During the addition a precipitate formed. After an additional 20 min at −70°, a solution of 42.1 ml (302 mmole) of triethylamine in 75 ml of dry dichloromethane was added over 15 min. The suspension was stirred for 45 min, the cooling bath was removed, and the reaction mixture allowed to reach room temperature (1.5 hr). Most of the dichloromethane was removed on a rotary evaporator under reduced pressure (room temperature bath) and the residue was equilibrated with 500 ml of water and 750 ml of ether. The aqueous phase was extracted 3 times with 750 ml of ether and the ether phases washed in a counter current manner with 500 ml of water to afford, after drying with $Na_2SO_4$, filtration, and evaporation under reduced pressure, 15.36 g of crude product. Medium pressure chromatography on silica gel using 4:1 hexanes-ether as the eluent (fractions collected under a nitrogen atmosphere) gave 14.95 g (94% yield) of [1R-[1α (S*),3aα,4β,7aβ]]-4-(acetyloxy)-octahydro-α,7a-dimethyl-1H-indene-1-acetaldehyde as a colorless oil.

EXAMPLE 4

[3aR-(1E,3aα,4β,7aβ)]-1-Ethylideneoctahydro-7a-methyl-1-H-inden-4-ol acetate

To a magnetically stirred solution of 2.0 g (7.95 mmole) of [1R [1α(S*),3aα,4β, 7aβ]]-4-(acetyloxy)-octahydro-β, 7a-dimethyl-1H-indene-1-acetaldehyde in 10 ml of ether under an argon atmosphere was added 100 mg of 10% palladium on charcoal. After 20 min. at ambient temperature, the suspension was filtered through a glass fiber filter circle. The filtrate was evaporated under reduced pressure on a rotary evaporator. To the residue was added 1.40 g (9.5 mmole) of benzalacetone (distilled) and 200 mg of 10% palladium on charcoal. The suspension was degassed by evacuating the flask and refilling with argon. Then the flask was partially immersed in a 230° C. oil bath for 30 min. After cooling, the contents of the flask were flash chromatographed on 100 g of silica gel to remove the more polar benzalacetone and its reduction product (benzylacetone) from the equilibrium mixture of $\Delta^{17E}$, $\Delta^{17Z}$, $\Delta^{16}$, and $\Delta^{20}$ indene olefins, which are present in a ratio of 65:4:27:4, respectively. Medium pressure chromatography on silver nitrate impregnated silica gel columns (two passes) separated the desired product ($\Delta^{17E}$) from to the less polar ($\Delta^{17Z}$, $\Delta^{16}$, and $\Delta^{20}$ in order of elution) olefins. Purification could be followed by tlc plates which were sprayed with a 10% solution of silver nitrate in acetonitrile and air dried before use. Thus, a total of 976 mg (55% yield) of [3aR-(1E,3aα, 4β,7aβ)]-1-ethylideneoctahydro-7a-methyl-1H-inden4-ol acetate was obtained as a colorless oil.

The more polar olefin mixture (420 mg., 24% yield) could be conveniently reequilibrated by addition to a subsequent aldehyde fragmentation reaction.

EXAMPLE 5

[3aS-[3(1R*,2R*S*,3aβ,7β,7aα)]-3a,4,5,6,7,7a-Hexahydro-3-[2-hydroxy-1-methyl-4-(trimethylsilyl)-3-butynyl]-3a-methyl-1H-inden-7-ol acetate.

A flame dried two-liter three-neck flask fitted with stirrer, dropping funnel, thermometer, and argon inlet was charged with 22.3 g (100 mmole) of [3aR-(1E,3aα,4β,7aβ)]-1-ethylideneoctahydro-7a-methyl-1H-inden-4-ol acetate and 300 ml of dry dichloro-methane. The solution was cooled to −20° with an acetone bath by addition of dry ice as necessary. At this point, the reagents were added incrementally. Initially, 200 ml (200 mmole) of 1M dimethyl-aluminum chloride in hexane was added rapidly dropwise over 5 min followed, after 10 min, by slow dropwise addition over 1 hr of 50 ml of a solution of 55.5 g (500 mmole) of 3-trimethylsilylpropynal diluted to 260 ml with dry dichloromethane. The addition of reagents was repeated in this manner 4 more times using 100 ml (100 mmole) of 1M dimethylaluminum chloride in hexane added rapidly followed by 50 ml of a solution of 3-trimethylsilyl- propynal added slowly over 1 hr. After the final addition, TLC (CH$_2$Cl$_2$óEt$_2$O, 98:2) confirmed the absence of starting olefin, and the reaction mixture was poured with vigorous stirring into 2 L of 20% Rochelle salt solution to which was added about 500 g of ice (final temperature was 200). The mixture was made alkaline by addition of 25 ml of 4 N sodium hydroxide, and 1 L of ether was added. The phases were separated and the ether phase was washed with 500 ml of brine. The aqueous phases were extracted in a counter current manner two times with 1.5 L of ether to afford, after drying with Na$_2$SO$_4$, filtration and evaporation under reduced pressure, 78 g of an oil. Medium pressure chromatography on silica gel was complicated by the difficulty of separating the products from a by-product, 4-trimethylsilyl-3-butyn-2-ol. Subsequently, advantage was taken of the volatility of the 4-trimethylsilyl-3-butyn-2-ol to remove it from the chromatographic fractions. Thus, there was obtained 25.54 g of more polar pure major isomer, 2.07 g of a 87:13 mixture (estimated by NMR) of major and minor isomers, and 0.53 g of pure minor isomer. The total yield of products was 79% (77% yield of the major isomer).

An analytical sample of the major isomer, [3aS-[3(1R*, 2S*,3aα,7β,7aα,]-3a,4,5,6,7,7a-hexahydro-3-[2-hydroxy-1-methyl-4-(trimethylsilyl)-3-butynyl]-3a-methyl-1H-inden-7-ol acetate, obtained as a white solid from ethyl acetate6hexane, m.p. 66–67°. An analytical sample of the minor isomer, [3aS-[3(1R*,2R*,3aβ,7β,7aα)]-3a,4,5,6,7,7a-hexahydro-3-[2-hydroxy-1-methyl-4-(tri-methylsilyl)-3-butynyl]-3a-methyl-1H-inden-7-ol acetate, obtained as a colorless oil.

EXAMPLE 6

[3aS-[(1S*,3aβ,7β,7aα)]-3a,4,5,6,7,7a-Hexahydro-3-[1-methyl-4-(trimethylsilyl)-3-butynyl]-3a-methyl-1H-inden-7-ol acetate To a magnetically stirred solution of 24.2 g (69 mmole) of [3aS-[3(1R*,2S*,3aβ,7β,7aα)]-3a,4,5,6,7,7a-hexahydro-3-[2-hydroxy-1-methyl-4-(trimethylsilyl)-3-butynyl]-3a-methyl-1H-inden-7-ol acetate in 300 ml of dry dichloromethane and 23.3 ml of dry pyridine was added 25.0 g (145 mmole) of phenyl chloro-thionoformate. A yellow amber color developed. The reaction mixture was stirred for 3 hr and then 10 ml of methanol was added. After 15 min, the reaction mixture was transferred to a separatory funnel containing 1 liter of ether. The ether phase was washed successively with 2×250 ml of 1 M phosphoric acid, 500 ml of water, and 500 ml of 1 M sodium bicarbonate. The aqueous phases were extracted in a counter current manner with 500 ml of ether. The combined ether phases were dried with Na$_2$SO$_4$, filtered, and evaporated under reduced pressure to give 47 g of crude product. Flash chromatography on 500 g of silica gel afforded 33.4 g (quantitative yield) of the thionocarbonate ester.

To a two-liter three-neck flask fitted with stirrer, dropping funnel, thermometer, and argon inlet charged with 33.4 g (69 mmole) of the above thioncarbonate ester in 500 ml of toluene was added rapidly dropwise, over 5 min 135 ml (500 mmole) of tri-n-butyltin hydride followed by 276 ml (276 mmole) of triethylborane over 15 min. After 1.3 hr, an additional 15 ml (56 mmole) of tri-n-butyltin hydride was added. After 50 min, the reaction mixture was poured into 500 ml of 10% sodium bicarbonate and 500 ml of ether was added. The aqueous phase was extracted two times with 500 ml of ether. The ether phases were washed in a countercurrent manner three times with 250 ml of water; and after drying with Na$_2$SO$_4$, filtration, and evaporation under reduced pressure, gave the crude product which was flash chromatographed on 500 g of silica gel. The product containing fractions in dichloromethane solution were washed with 10% sodium carbonate to remove the phenol formed in the reaction. Medium pressure chromatography required several passes to remove the by products and afforded 16.13 g (70%) of pure [3aS-[(1S*,3aβ,7β,7aα)]-3a,4,5,6,7,7a-hexahydro-3-[1-methyl-4-(trimethylsilyl)-3-butynyl]-3a-methyl-1H-inden-7-ol acetate as a colorless oil.

EXAMPLE 7

[3aS-[1(S*),3aβ,7β,7aα)]-3a,4,5,6,7,7a-Hexahydro-3-[1-methyl-3-butynyl]-3a-methyl-1H-inden-7-ol To a solution of 5.01 g (15 mmole) of [3aS-[(1S*,3aβ, 7β,7aα)]3a,4,5,6,7,7a-hexahydro--3-[1-methyl-4-

(trimethylsilyl)-3-butynyl]-3a-methyl-1H-inden-7-ol acetate in 50 ml of ethanol was added 30 ml (60 mmole) of 2N sodium hydroxide and heated at 80° C. for four hours. It was then diluted with 500 ml water-brine (1:1), and thoroughly extracted with ethyl acetate. The combined extracts were washed with water and brine, dried over sodium sulfate and evaporated to dryness. The crude product was purified by FLASH chromatography with hexane-ethyl acetate (4:1) to give 3.14 g (95.4%) of the title compound.

EXAMPLE 8

[3aS-[1(S*),3aβ,7β,7aα)]-3a,4,5,6,7,7a-Hexahydro-3-[1-methyl-3-butynyl]-3a-methyl-7-[(trimethylsilyl)oxy]-1H-indene To a solution of 3.14 g (14.4 mmole) of [3aS-[1(S*),3aβ,7β,7aα)]-3a,4,5,6,7,7a-hexahydro-3-[1-methyl-3-butynyl]-3a-methyl-1H-inden-7-ol in 30 ml of anhydrous methylene chloride was added 4.22 ml (28.8 mmole) of 1-(trimethylsilyl)imidazole, and the reaction mixture was stirred at room temperature for 1 hour. It was then quenched by addition of crushed ice and stirring for 15 minutes. After dilution with water and brine, it was thoroughly extracted with hexane. The combined extracts were washed with water and brine, dried over sodium sulfate and evaporated to dryness. The crude product was purified by FLASH chromatography with hexane-methylene chloride (40:1), to give 3.55 g (85%) of the title compound.

EXAMPLE 9

[1(S*),3aR-3aα,4β,7aβ)]-3a,4,5,6,7,7a-Hexahydro-1-(1,5-dimethyl-5-hydroxy-3-hexynyl)-7a-methyl-4-[(trimethylsilyl)oxy]-3H-indene To a solution of 612 mg (2.10 mmole) of [3aS-[1(S*),3aβ,7β,7aα]3a,4,5,6,7,7a-hexahydro-3-[1-methyl-3-butynyl]-3a-methyl-7-[(trimethylsilyl)oxy]-1H-indene in 15 ml of anhydrous ether at −78° C. was added 1.6 ml (2.52 mmole) of 1.6 M n-butyllithium in hexane under an argon atmosphere. After stirring for 1 hour at −78° C., 1.5 ml (21 mmole) of anhydrous acetone was added and the stirring was continued for 1 hour. The reaction was quenched with water-brine (1:1) and extracted thoroughly with ethyl acetate. The combined extracts were washed with water and brine, dried over sodium sulfate and evaporated to dryness. Separation by FLASH chromatography with hexane-ethyl acetate (9:1) regenerated 166 mg (27%) of starting material, and gave 521 mg (71%) of the title compound.

EXAMPLE 10

[1(S*),3aR-(3aα,4β,7aβ)]-3a,4,5,6,7,7a-Hexahydro-1-(1,5-dimethyl-5-hydroxy-3-hexynyl)-7a-methyl-3H-inden-4-ol To a stirred solution of 521 mg (1.50 mmole) of [1(S*),3aR-(3aα,4β,7aβ]-3a, 4,5,6,7,7a-hexahydro-1-[1,5-dimethyl-5-hydroxy-3-hexynyl)-7a-methyl-4-[(trimethylsilyl)oxy]-3H-indene in 10 ml of anhydrous tetrahydrofuran was added 3 ml (3 mmole) of 1 M tetrabutylammonium fluoride. The mixture was stirred at room temperature for 1.5 hours, then diluted with water and brine and extracted thoroughly with ethyl acetate. The combined extracts were washed with water and brine, dried over sodium sulfate and evaporated to dryness. The crude product was crystalline. It was recrystalized from hexane to give 360 mg (87%) of the title compound, m.p. 115–116° C. (from hexane).

EXAMPLE 11

[1(S*),3aR-(3aα,7aβ)]-3,3a,5,6,7,7a-Hexahydro-1-(1,5-dimethyl-5-hydroxy-3-hexynyl)-3-7a-methyl-4H-inden-4-one To a solution of 240 mg (0.868 mmole) of [1(S*),3aR-(3aα,4β,7aβ)]-3a,4,5,6,7,7a-hexahydro-1-[1,5-dimethyl-5-hydroxy-3-hexynyl)-7a-methyl-3H-inden-4-ol in 7 ml of anhydrous methylene chloride was added 980 mg (2.6 mmole) of pyridinium dichromate. This mixture was stirred at room temperature for 2 hours, then additional 500 mg (1.33 mmole) of pyridinium dichromate was added, and stirring was continued for 2.25 hours. After addition of 30 ml ether and stirring for 15 min, the mixture was filtered through Celite, and the Celite pad was washed with 3×50 ml of ethyl acetate. The combined filtrates were washed with 20 ml 1N HCl, water, 40 ml 2N potassium bicarbonate, and a mixture of water and brine 1:1. The aqueous layers were reextracted with 2×100 ml ethyl acetate. The combined organic layers were dried over sodium sulfate and evaporated to dryness. The crude product was purified by FLASH chromatography with hexane-ethyl acetate 2:1, to give 214 mg (89%) of the title compound.

EXAMPLE 12

[1(S*),3aR-(3aα,7aβ)]-3,3a,5,6,7,7a-Hexahydro-1-(1,5-dimethyl-5-[(trimethylsilyl)oxy]-3-hexynyl)-7a-methyl-4H-inden-4-one To a solution of 214 mg (0.78 mmole) of [1(S*),3aR-(3aα,7β)]-3,3a,5,6,7,7a-hexahydro-1-(1,5-dimethyl-5-hydroxy-3-hexynyl)-7a-methyl-4H-inden-4-one in 7 ml of anhydrous methylene chloride was added 750 mg (4.7 mmole) of 1-(trimethylsilyl)-imidazole. The mixture was stirred for 17 hours at room temperature in an argon atmosphere, and then quenched with 5 ml of water and stirred for 20 min. It was then extracted with 3×100 ml ethyl acetate. The extracts were combined and washed with 5×50 ml of water and brine mixture, dried over sodium sulfate and evaporated to dryness. The crude product was purified by FLASH chromatography with hexane-ethyl acetate (12:1) to give 255 mg (94%) of the title compound.

EXAMPLE 13

1,25-Dihydroxy-16-ene-23-yne-20-epi-cholecalciferol

To a stirred solution of 730 mg (1.25 mmole) of [3S-(1Z,3α,5β)]-[2-[3,5-bis[[1,1-dimethylethyl)dimethylsilyl]oxy]-2-methylene-cyclohexylidene]ethyl]diphenylphosphine oxide, a known compound, in 7 ml anhydrous tetrahydrofuran at −78° C. was added 0.78 ml (1.25 mmole) of 1.6M n-butyllithium in hexane dropwise in an argon atmosphere. After stirring for 5 min, to the thus obtained red colored solution was added dropwise a solution of 255 mg (0.736 mmole) of [1(S*),3aR-(3aα,7aβ)]-3,3a,5,6,7,7a-hexahydro-1-(1,5-dimethyl-5-[(trimethylsilyl)oxy]-3-hexynyl)-7a-methyl-4H-inden-4-one in 4.5 ml anhydrous tetrahydrofuran over a 10 min period, and the reaction mixture was stirred at −78° C. for 90 min. The reaction was then quenched by addition of 10 ml of a 1:1 mixture of 2N Rochelle salt and 2N potassium bicarbonate and was allowed to warm up to room temperature. Additional 30 ml of Rochelle salt/potassium bicarbonate solutions were added and the reaction mixture was extracted with 3×100 ml ethyl acetate. The extracts were washed three times with brine, dried over sodium sulfate and evaporated to dryness. The crude product was purified by FLASH chromatography with hexane-ethyl acetate 40:1 to give 467 mg (89%) of the trisilylated intermediate.

To the solution of the trisilylated intermediate (467 mg) in 4.5 ml anhydrous tetrahydrofuran was added 7 ml (7 mmole) of a 1M tetrabutylammonium fluoride in tetrahydrofuran, and this mixture was stirred at room temperature in argon atmosphere for 17 hours. The reaction was then quenched by addition of 5 ml water and stirring for 20 min. Tetrahydrofuran was then removed in vacuum, the residue was diluted with water and extracted with 3×100 ml ethyl acetate. The extracts were washed with water and brine, dried over sodium sulfate and evaporated to dryness. The crude product was purified by FLASH chromatography with hexane-ethyl acetate 1:5 to give 250 mg (83%) of crystalline title compound. It was recrystallized from 1.5 ml tetrahydrofuran by addition of 7 ml methyl formate; m.p. 148–149° C.

EXAMPLE 14

[1(S*),3aR-(3aα,4β,7aβ)]-3a,4,5,6,7,7a-Hexahydro-1-(1,5-dimethyl-5-hydroxy-3Z-hexenyl)-7a-methyl-3H-inden4-ol A mixture of 1.02 g (3.6 mmole) of [1(S*),3aR-(3aα,4β,7aβ)]-3a,4,5,6,7,7a-hexahydro-1-(1,5-dimethyl-5-hydroxy-3-hexynyl)-7a-methyl-3H-inden-4-ol, 13.5 ml ethyl acetate, 34 ml hexane, 1.3 ml absolute ethanol, 0.067 ml quinoline and 225 mg Lindlar catalyst was hydrogenated at room temperature for 3.5 hours. The reaction mixture was filtered through a Celite pad, which was subsequently washed with ethyl acetate. The combined filtrates were washed with 1N HCl, water, 2N potassium bicarbonate, water and brine, dried over sodium sulfate and evaporated to dryness. The crude product was purified by preparative HPLC using YMC column—silica gel with hexane-ethyl acetate 3:2. It gave 954 mg (92.6%) of the title compound, m.p. 88–90° C. (from $CH_2Cl_2$-hexane).

EXAMPLE 15

[1(S*),3aR-(3aα,4β,7aβ)]-3a,4,5,6,7,7a-Hexahydro-1-(1,5dimethyl-5-hydroxy-hexanyl)-7a-methyl-3H-inden-4-ol To a solution of 601 mg (2.16 mmole) of [1(S*),3aR-(3aα,4β,7aβ)]-3a,4,5,6,7,7a-hexahydro-1-(1,5-dimethyl-5-hydroxy-3Z-hexenyl)-7a-methyl-3H-inden-4-ol in 35 ml anhydrous methylene chloride was added 120 mg of 1,4-bis(diphenyl-phospheno)butane1,5-cyclooctadiene rhodium tetrafluoroborate and one drop of mercury and then hydrogenated using Paar apparatus at room temperature and 50 p.s.i. pressure for 1.25 hours. TLC hexane-ethyl acetate 3:2 showed that the reaction was complete. The reaction mixture was filtered through a Celite pad, which was then washed with ethyl acetate. The combined filtrates were evaporated to dryness. Purification was done by FLASH chromatography with hexane-ethyl acetate 3:2, and then by preparative HPLC using YMC silica gel column with hexane-ethyl acetate 3:2, 100 ml/min. It gave 550 mg (91%) of crystalline title compound.

EXAMPLE 16

[1(S*),3aR(3aα,7aβ)]-3,3a,5,6,7,7a-Hexahydro-1-(1,5-dimethyl-5-hydroxy-hexanyl)-7a-methyl-4-inden-4-one To a solution of 270 mg (0.963 mmole) of [1(S*),3aR-(3aα,4β,7aβ)]-3a,4,5,6,7,7a-hexahydro-1-(1,5-dimethyl-5-hydroxy-hexanyl)-7a-methyl-3H-inden-4-ol in 7 ml of anhydrous methylene chloride was added 1.58 g (4.2 mmole) of pyridinium dichromate. The reaction mixture was stirred at room temperature for 4.75 hrs. It was then diluted with 25 ml of ether, stirred for additional 15 min, and filtered through a Celite pad. The pad was washed with 3×50 ml of ether. The combined filtrates were washed with 40 ml of 2N potassium bicarbonate and water-brine mixture. The aqueous layers were extracted with 2×90 ml of ethyl acetate. The combined organic layers were dried over sodium sulfate and evaporated to dryness. The crude product was purified by FLASH chromatography with hexane-ethyl acetate (2:1) to give 254 mg (95%) of the title compound.

EXAMPLE 17

[1(S*),3aR(3aα,7aβ)]-3,3a,5,6,7,7a-Hexahydro-1-(1,5-dimethyl-5-[(trimethylsilyl)oxy]-hexanyl)-7a-methyl-4H-inden-4-one To a solution of 254 mg (0.912 mmole) of [1(S*),3aR-(3aα,7β)]-3,3a,5,6,7,7a-hexahydro-1-(1,5-dimethyl-5-hydroxy-hexanyl)-7a-methyl-4H-inden-4-one in 6 ml of anhydrous methylene chloride was added 0.8 ml (5.45 mmole) of 1-(trimethylsilyl)-imidazole. The reaction mixture was stirred at room temperature under argon for 4.25 hrs. It was quenched then by addition of 5 ml of water and stirring for 20 min., and extracted with 3×90 ml of ethyl acetate. The extracts were washed with water and brine, dried over sodium sulfate and evaporated to dryness. The crude product was purified by FLASH chromatography with hexane-ethyl acetate (12:1) to give 308 mg (96%) of the title compound.

EXAMPLE 18

1,25-Dihydroxy-16-ene-20-epi-cholecalciferol

To a stirred solution of 850 mg (1.46 mmole) of [3S-(1Z,3α,5β)]-[2-[3,5-bis[[(1,1-dimethylethyl)dimethylsilyl]oxy]-2-methylene-cyclohexylidene]-ethyl]diphenylphosphine oxide in 9 ml of anhydrous tetrahydrofuran at −78° C. was added 0.91 ml (1.46 mmole) of 1.6M n-butyllithium in hexane dropwise in an argon atmosphere. After stirring for 5 min, to thus obtained red colored solution was added dropwise a solution of 308 mg (0.878 mmole) of [1(S*),3aR-3aα,7aβ)]-3,3a,5,6,7,7a-hexahydro-1-(1,5-dimethyl-5-[(trimethylsilyl)oxy]-hexanyl)-7a-methyl-4H-inden-4-one in 4.5 ml of anhydrous tetrahydrofuran over a 10 min period. The reaction mixture was stirred at −78° C. for 2 hours and then quenched by addition of 10 ml of 1:1 mixture of 2N Rochelle salt and 2N potassium bicarbonate and by warming up to room temperature. After addition of 30 ml of Rochelle salt/potassium bicarbonate, the mixture was extracted with 3×100 ml of ethyl acetate. The combined extracts were washed with brine, dried over sodium sulfate and evaporated to dryness. The residue was purified by FLASH chromatography with hexane-ethyl acetate 50:1 to give 541 mg of silylated intermediate.

To the solution of this intermediate in 5 ml of anhydrous tetrahydrofuran was added 5.5 ml (5.5 mmole) of 1 M tetrabutyl ammonium fluoride in tetrahydrofuran and the solution was stirred at room temperature under argon for 23 hours. The reaction was quenched with 5 ml of water and stirring for 20 min. After addition of 25 ml brine, it was extracted with 3×100 ml of ethyl acetate. The combined extracts were washed with water and brine, dried over sodium sulfate and evaporated to dryness. The crude product was first purified by FLASH chromatography with hexane-ethyl acetate (1:9), and then by HPLC (YMC silica gel column) with ethyl acetate to give 296 mg (81%) of crystalline title compound, m.p. 124–125° C. (methyl formate).

EXAMPLE 19

[3aR-[1(S*),3aα,4β,7aβ]]-3,3a,5,6,7,7a-Hexahydro-7a-methyl-1-[6,6,6-trifluoro-5-hydroxy-1-methyl-5-(trifluoromethyl)-3-hexynyl]4-[(trimethylsilyl)oxy]-3H-indene In a 100 ml heart-shaped flask fitted with a gas inlet was placed a solution of 1 g (3.44 mmole) of [3aS-[1(S*),3aβ,7β,7aα]-3a,4,5,6,7,7a-hexahydro-3-[1-methyl-3-butynyl]-3a-methyl-7-[(trimethyl-silyl)oxy]-1H-indene in 25 ml anhydrous tetrahydrofuran. After cooling at −78° C., 3.2 ml (5.16 mmole) of 1.6M n-butyllithium in hexane was added dropwise over a 10 minute period, and the resulting mixture was stirred for 30 minutes. After adding 10 ml anhydrous tetrahydrofuran, a stream of hexafluoroacetone was bubbled into the mixture for one minute. After 1 hour and 15 minutes of stirring TLC showed that the reaction was about 70% complete. At this point the reaction was quenched by addition of 25 ml saturated brine, following by warming to room temperature. It was then extracted with hexane. The combined organic extracts were washed with brine, dried over sodium sulfate and evaporated to dryness. Purification of the crude product was done by FLASH chromatography with hexane-ethyl acetate (10:1). This gave 270 mg (27%) of starting material and 1.15 g (73%) of the title compound.

In the second experiment, to the solution of the starting acetylene 1.38 g (4.75 mmole) in 20 ml of anhydrous tetrahydrofuran at −78° C. in argon atmosphere was added dropwise over 10 min, 4.5 ml (7.2 mmole) of 1.6M n-butyllithium in hexane. After stirring for 30 min, hexafluoroacetone was bubbled at a slow rate for 2 min, stirred for 30 min, bubbled for an additional minute, stirred for 60 min, and finally bubbled for 30 sec and stirred for 30 minutes. At this time TLC showed the reaction complete. In this experiment the reaction was quenched with 2N Rochelle salt, and the purification by FLASH chromatography was with hexane-ethyl acetate (14:1). It gave 1.97 g (91%) of the title compound.

EXAMPLE 20

[3aR-[1(S*),3aα,4β,7aβ]]-3,3a,5,6,7,7a-Hexahydro-7a-methyl-1-[6,6,6-trifluoro-5-hydroxy-1-methyl-5-(trifluoromethyl)-3-hexynyl]-4-ol To a solution of 1.17 g (2.56 mmole) of [3aR-[1(S*),3aα,4β,7aβ]]-3,3a,5,6,7,7a-hexahydro-7a-methyl-1-[6,6,6-trifluoro-5-hydroxy-1-methyl-5-(trifluoromethyl)-3-hexynyl]-4-[(trimethysilyl)oxy]-3H-indene in 20 ml anhydrous tetrahydrofuran was added 7.12 ml (7.12 mmole) of 1M tetrabutyl ammonium fluoride in tetrahydrofuran and stirred in argon atmosphere for 3.5 hours. The reaction mixture was then diluted with 250 ml of water-brine 1:1 mixture, and extracted thoroughly with ethyl acetate. The extracts were washed with water and brine, dried over sodium sulfate and evaporated to dryness. Purification of the crude product was done by FLASH chromatography to give 946 mg (96%) of the title compound; m.p. 75–76° C. after recrystalization from hexane.

EXAMPLE 21

[1(S*), 3aR-(3aα,7aβ)-3,3a,5,6,7,7a-Hexahydro-7a-methyl-1-[6,6,6-trifluoro-5-hydroxy-1-methyl-5-(trifluoromethyl)-3-hexynyl]-4H-inden4-one To a solution of 284 mg (0.74 mmole) of [3aR-[1(S*)-3aα,4β,7aβ]]-3,3a,5,6,7,7a-hexahydro-7a-methyl-1-[6,6,6-trifluoro-5-hydroxy-1-methyl-5-(trifluoromethyl)-3-hexynyl]-3H-inden-4-ol in 10 ml of anhydrous methylene chloride was added in portions 2.15 g (5 mmole) of pyridinium dichromate and the reaction mixture was stirred at room temperature for 5 hours. After addition of 50 ml of ether and stirring for 15 minutes, the reaction mixture was filtered through Celite pad, which was subsequently washed with 3×50 ml of ethyl acetate. The combined filtrates were washed with 2N Hcl, water, 2N potassium bicarbonate, water and brine, dried over sodium sulfate, and evaporated to dryness. The crude product was purified by FLASH chromatography with hexane-ethyl acetate (3:1), to give 259 mg (91%) of the crystalline title compound.

EXAMPLE 22

1,25-Dihydroxy-16-ene-23-yne-26,27-hexafluoro-20-epi-cholecalciferol

To a stirred solution of 987 mg (1.69 mmole) of [3S-(1Z, 3α,5β)]-[2-[3,5-bis[[(1,1-dimethylethyl)dimethylsilyl]oxy]-2-methylene-cyclohexylidene]ethyl]diphenylphosphine oxide in 10 ml of anhydrous tetrahydrofuran at −78° C. was added 1.05 ml (1.69 mmole) of 1.6M n-butyllithium in hexane dropwise in an argon atmosphere. After stirring for 15 minutes, to thus obtained red colored solution was added dropwise a solution of 259 mg (0.677 mmole) of [1(S*),3aR-(3aα,7aβ)-3,3a,5,6,7,7a-hexahydro-7a-methyl-1[6,6,6-trifluoro-5-hydroxy-1-methyl-5-(trifluoro-methyl)-3-hexynyl]-4H-inden-4-one in 5 ml anhydrous tetrahydrofuran, and thus obtained reaction mixture was stirred at −78° C. for 1 hour. The reaction was then quenched by addition of 2N Rochelle salt solution and by allowing to warm up to room temperature. After addition of saturated brine, it was extracted thoroughly with ethyl acetate. The combined extracts were washed with water and brine, dried over sodium sulfate and evaporated to dryness. The residue was purified by FLASH chromatography with hexane-ethyl acetate (9:1) to give 370 mg of intermediate disilyl ether.

To the solution of this intermediate (370 mg) in 10 ml of anhydrous tetrahydrofuran was added 3 ml (3 mmole) of a 1M tetrabutyl-ammonium fluoride in tetrahydrofuran, and thus obtained reaction mixture was stirred at room temperature overnight. It was then diluted with water and brine and extracted thoroughly with 4×50 ml of ethyl acetate. The combined extracts were washed with water and brine, dried over sodium sulfate, and evaporated to dryness. The crude product was purified by FLASH chromatography with hexane-ethyl acetate (1:4) to give 249 mg (71%) of the title compound as a foam.

EXAMPLE 23

[3aR-[1(S*),3aα,4β,7aβ]]-3a,4,5,6,7,7a-Hexahydro-7a-methyl-1-[6,6,6-trifluoro-5-hydroxy-1-methyl-5-(trifluoromethyl)-3E-hexenyl]-3H-inden-4-ol To a under argon stirred suspension of 165 mg (4.34 mmole) lithium aluminum hydride in 15 ml anhydrous tetrahydrofuran, cooled in an ice-bath, was first added 235 mg (4.34 mmole) of solid sodium methoxide, and then dropwise 334 mg (0.87 mmole) of [3aR-1(S*)-3aα,4β,7aβ]]-3a,4,5,6,7,7a-hexahydro-7a-methyl-1-[6,6,6-trifluoro-5-hydroxy-1-methyl-5-(trifluoromethyl)-3-hexynyl]-3H-inden-4-ol dissolved in 10 ml of anhydrous tetrahydrofuran. The thus obtained reaction mixture was heated under reflux (80° C.) for 2.5 hours, when TLC indicated that the reaction was complete. The mixture was cooled in an ice-bath, and then quenched carefully with 1 ml of water and 1 ml 2N sodium hydroxide. After addition of 20 ml of ether, it was stirred 0.5 hour, 2.2 g magnesium sulfate was added, stirred for 0.5 hour, filtered and evaporated to dryness. It gave 335 mg (100%) of crystalline title compound (TLC pure).

EXAMPLE 24

[1(S*),3aR-(3aα,7aβ)-3,3a,5,6,7,7a-Hexahydro-7a-methyl-1-[6,6,6-trifluoro-5-hydroxy-1-methyl-5-(trifluoromethyl)-3E-hexenyl]-4H-inden-4-one To a solution of 256 mg (0.66 mmole) of [3aR-[1(S*),3aα,4β,7aβ]]-3a,4,5,6,7,7a-hexahydro-7a-methyl-1-[6,6,6-trifluoro-5-hydroxy-1-methyl-5-(trifluoromethyl)-3E-hexenyl]-3H-inden-4-ol in 10 ml of anhydrous methylene chloride was added in portions 1.12 g (3 mmole) of pyridinium dichromate, and the reaction mixture was stirred at room temperature for 4 hours. After addition of 25 ml of ether and stirring for 15 minutes, the reaction mixture was filtered through a 10 Celite pad, which was subsequently washed with 3×20 ml of ethyl acetate. The combined filtrates were washed with 2N potassium bicarbonate, water and brine, dried over sodium sulfate and evaporated to dryness. The crude product was purified by FLASH chromatography with methylene chloride-ethyl acetate (9:1) to give 230 mg (90%) of crystalline title compound.

EXAMPLE 25

[1(S*),3aR-(3aα,7aβ)-3,3a,5,6,7,7a-Hexahydro-7a-methyl-1-[6,6,6-trifluoro-5-(trimethylsilyl)oxy-1-methyl-5-trifluoromethyl)-3E-hexenyl]4H-inden-4-one To a stirred solution of 268 mg (0.697 mmole) of [1(S*),3aR-(3aα,7aβ)-3,3a,5,6,7,7a-hexahydro-7a-methyl-1-[6,6,6-trifluoro-5-hydroxy-1-methyl-5-(trifluoromethyl)-3E-hexenyl]4H-inden-4-one in 8 ml of anhydrous methylene chloride at room temperature was added 0.92 ml (6.27 mmole) of 1-(trimethyl-silyl)-imidazole, and the reaction mixture was stirred at room temperature overnight. The reaction mixture was then diluted with water and extracted thoroughly with hexane. The combined extracts were washed with water and brine to neutrality, dried over sodium sulfate and evaporated to dryness. The crude product was purified by FLASH chromatography with hexane-ethyl acetate 9:1 to give 310 mg (97%) of the title compound.

EXAMPLE 26

1,25-Dihydroxy-16,23E-diene-26,27-hexafluoro-20-epi-cholecalciferol

To a stirred solution of 725 mg (1.24 mmole) of [3S-(1Z,3α,5β)]-[2-[3,5-bis[[(1,1-dimethylethyl)dimethylsilyl]oxy]-2-methylene cyclohexylidene]ethyl ]diphenylphosphine oxide in 15 ml of anhydrous tetrahydrofuran at −78° C. was added 0.78 ml (1.24 mmole) of 1.6M n-butyllithium in hexane dropwise in an argon atmosphere. After stirring for 5 min, to thus obtained red colored solution was added dropwise a solution of 307 mg (0.672 mmole) of [1(S*),3aR (3aα,7aβ)-3,3a,5,6,7,7a-hexahydro-7a-methyl-1-[6,6,6-trifluoro-5-(trimethylsilyl)oxy-1-methyl-5-(trifluoromethyl)-3E-hexenyl]4H-inden-4-one in 9 ml of anhydrous tetrahydrofuran. The reaction mixture was stirred at −78° C. for 2.5 hrs and then quenched with water and allowed to warm up to room temperature. After further dilution with water, it was extracted with 3×30 ml ethyl acetate. The combined extracts were washed with water and brine, dried over sodium sulfate and evaporated to dryness. Thus obtained disilyl ether intermediate was purified by FLASH chromatography with hexane-ethyl acetate 9:1 to give 449 mg of pure intermediate (the 25-silyloxy group was hydrolyzed during the reaction).

To the solution of this intermediate (449 mg) in 10 ml anhydrous tetrahydrofuran was added 3.6 ml (3.6 mmole) of a 1M tetrabutyl ammonium fluoride in tetrahydrofuran and thus obtained reaction mixture was stirred at room temperature overnight. The reaction was quenched with ice, stirred 15 min, diluted with water and brine, and extracted with ethyl acetate. The combined extracts were washed with water, dried over sodium sulfate and evaporated to dryness. The crude product was purified by FLASH chromatography with hexane-ethyl acetate (1:2) to give the title compound as white foam, 291 mg (83%).

EXAMPLE 27

[3aR-[1(S*),3aα,4β,7aβ]]-3,3a,5,6,7,7a-Hexahydro-7a-methyl-1-[6,6,6-inden-4-ol

A mixture of 1.62 g (4.21 mmole) of [3aR-1(S*)-3aα,4β,7aβ]]-3,3a,5,6,7,7a-hexahydro-7a-methyl-1-[6,6,6-trifluoro-5-hydroxy-1-methyl-5-(trifluoromethyl)-3-hexynyl]-3H-inden-4-ol, 16 ml of ethyl acetate, 40 ml of hexane, 1.6 ml of absolute ethanol, 0.080 ml of quinoline and 320 mg of Lindlar catalyst was stirred under hydrogen atmosphere for 70 min at room temperature. It was then filtered over Celite and the filter cake was washed with 3×60 ml of ethyl acetate. The filtrate was washed with 25 ml of 1N HCl and 4 times with a mixture of water and brine. The aqueous layers were extracted with 2×90 ml of ethyl acetate. The combined organic layers were dried over sodium sulfate and evaporated to dryness. The crude product was purified by HPLC YMC 50 mm×50 cm silica gel column with hexane-ethyl acetate (3:1), flow 100 ml/min to give 1.51 g (93%) of the title compound as white solid.

EXAMPLE 28

[1(S*),3aR-(3aα,7aβ)-3,3a,5,6,7,7a-Hexahydro-7a-methyl-1-[6,6,6-trifluoro-5-hydroxy-1-methyl-5-(trifluoromethyl)-3Z-hexenyl]4H-inden-4-one To a solution of 750 mg (1.94 mmole) of [3aR-[1(S*),3aβ,4β,7aβ]]-3,3a,5,6,7,7a-hexahydro-7a-methyl-1-[6,6,6-trifluoro-5-hydroxy-1-methyl-5-(trifluoromethyl)-3Z-hexenyl]-3H-inden-4-ol in 14 ml methylene chloride was added, in portions, 3.64 g (9.68 mmole) of pyridinium dichromate, and the reaction mixture was stirred at room temperature for 5 hours. To the reaction mixture was then added 30 ml of ether, stirred for 15 minutes, filtered through a Celite pad and the pad was washed with 3×50 ml of ether. The combined filtrates were washed with 2N potassium bicarbonate (50 ml) and three times with water and brine 1:1. The aqueous layers were extracted with 2×100 ml of ethyl acetate. The combined organic layers were dried over sodium sulfate and evaporated to dryness. The crude product was purified by FLASH chromatography with hexane-ethyl acetate to give 720 mg (96.5%) of the title compound as white solid.

EXAMPLE 29

[1(S*),3aR-(3aα,7aβ)-3,3a,5,6,7,7a-Hexahydro-7a-methyl-1-[6,6,6-trifluoro-5-trimethylsilyloxy-1-methyl-5-trifluoromethyl-3Z-hexenyl]4H-inden-4-one To a stirred solution of 720 mg (1.87 mmole) of [1(S*),3aR-(3aα,7aβ)-3,3a,5,6,7,7a-hexahydro-7a-methyl-1-[6,6, 6-trifluoro-5-hydroxy-1-methyl-5-trifluoromethyl-3Z-hexenyl]-4H-inden-4-one in 13 ml of anhydrous methylene chloride at room temperature was added 1.86 ml (12.68 mmole) of 1-trimethylsilyl-imidazole, and the reaction mixture was stirred under argon atmosphere for 17 hours. The reaction was then quenched with 7 ml water and stirring for 15 min., 20 ml of brine was added and extracted with 3×100 ml of ethyl acetate. The combined extracts were washed five times with water and brine, dried over sodium sulfate and evaporated to dryness. The crude product was purified by FLASH chromatography with hexane-ethyl acetate (9:1) to give 825 mg (96.5%) of the amorphous title compound.

EXAMPLE 30

1,25-Dihydroxy-16,23Z-diene-26,27-hexafluoro-20-epi-cholecalciferol

To a stirred solution of 555 mg (0.952 mmole) of [3S-(1Z,3α,5β)]-[2-[3,5-bis[[(1,1-dimethylethyl)dimethylsilyl]oxy]-2-methylenecyclohexylidene]ethyl]diphenyl-phosphine oxide in 6 ml of anhydrous tetrahydrofuran at −78° C. was added 0.595 ml (0.952 mmole) of 1.6M n-butyllithium in hexane dropwise in an argon atmosphere. After stirring for 5 min, to the thus obtained red colored solution was added dropwise a solution of 270 mg (0.591 mmole) of [1(S*),3aR-(3aα,7aβ)-3,3a,5,6,7,7a-hexahydro-7a-methyl-1-[6,6,6-trifluoro-5-trimethylsilyloxy-1-methyl-5-trifluoromethyl-3Z-hexenyl]-4H-inden-4-one in 4 ml of anhydrous tetrahydrofuran over a 10 min period. The reaction mixture was stirred at −78° C. for 1.75 hours, and then was quenched by addition of 10 ml of 2N Rochelle salt and by warming up to room temperature. It was then diluted with 30 ml of 2N Rochelle salt and extracted with 3×100 ml of ethyl acetate. The combined extracts were washed three times with brine, dried over sodium sulfate and evaporated to dryness. The crude silylated intermediate was purified by FLASH chromatography with hexane-ethyl acetate (10:1) to give 355 mg of pure intermediate.

To the solution of this intermediate in 4 ml of anhydrous tetrahydrofuran was added 3.8 ml (3.8 mmole) of 1M tetrabutyl ammonium fluoride in tetrahydrofuran under argon, and the reaction mixture was stirred at room temperature for 19 hours. The reaction was then quenched with 5 ml water and stirring for 15 min. After dilution with 20 ml of brine, it was extracted with 3×90 ml of ethyl acetate. The combined extracts were washed 4 times with mixture of water and brine, dried over sodium sulfate and evaporated to dryness. The crude product was purified by FLASH chromatography with hexane-ethyl acetate (1:3), to give 237 mg (77%) of crystalline title compound; m.p. 120–122° C. (from tetrahydrofuran-methylformate recrystallization).

EXAMPLE 31

1,25-Dihydroxy-16,23Z-diene-26,27-hexafluoro-20-epi-19-nor-cholecalciferol

A solution of 700 mg (1.23 mmole) of [3R-(3α,5β,Z)-3,5-bis[[(1,1-dimethylethyl) dimethylsilyl]oxy] cyclohexylidene]ethyl]diphenyl-phosphine oxide in 7 ml of anhydrous tetrahydrofuran was cooled in a dry ice bath to −78° C. and treated with 0.77 ml (1.23 mmole) of 1.6M n-butyllithium in hexane and stirred for 5 min. under an argon atmosphere. To this was added dropwise in the course of 10 min. a solution of 277 mg (0.607 mmole) of [1(S*), 3aR-(3aα,7aβ)-3,3a,5,6,7,7a-hexahydro-7a-methyl-1-[6,6,6-trifluoro-5-trimethylsilyloxy-1-methyl-5-trifluoromethyl-3Z-hexenyl]-4H-inden-4-one in 4 ml of anhydrous tetrahydrofuran. Thus obtained reaction mixture was stirred at −78° C. for 2 hours. After addition of 10 ml of 2N Rochelle Salt, it was warmed up to room temperature. After further dilution with 25 ml of 2N Rochelle Salt, it was extracted with 3×100 ml of ethyl acetate. The organic layers were washed w residue was chromatographed on a silica gel column with hexane-ethyl acetate (10:1), followed by elution with hexane-ethyl acetate (1:3) to recover the ring A precursor. It gave 329 mg of the ring A disilylated title compound.

To the solution of 329 mg disilylated title compound in 2.5 ml of anhydrous tetrahydro-furan was added 4.4 ml (4.4 mmole) of 1 M tetrabutylammonium fluoride in tetrahydrofuran, and the reaction mixture was stirred at room temperature for 65 hours. It was then quenched with 10 ml water, stirred for 15 min., 20 ml of brine was added and extracted with 3×90 ml of ethyl acetate. The combined organic layers were washed with water and brine, dried over sodium sulfate and evaporated to dryness. The crude product was first purified by FLASH chromatography with hexane-ethyl acetate (1:8), and then by HPLC on a YMC (50 cm×50 mm) silica gel column, to give 210 mg (68%) of the title compound as white foam.

EXAMPLE 32

1α-Fluoro-25-hydroxy-16,23Z-diene-26,27-hexafluoro-20-epi-cholecalciferol

To a solution of 460 mg (0.977 mmole) [3S-(3α,5β,Z)]-2-[2-[2 methylene-3-fluoro -5-[[(1,1-dimethylethyl) dimethylsilyl]oxy]cyclohexylidene]ethyl]diphenyl phosphine oxide in 6 ml of anhydrous tetrahydrofuran at −78° C. was added 0.61 ml (0.976 mmole) of 1.6M n-butyllithium in hexane dropwise in an argon atmosphere. After stirring for 5 min., a solution of 277 mg (0.607 mmole) of [1(S*),3aR-(3aα,7aβ)-3,3a,5,6,7,7a-hexahydro-7a-methyl-1-[6,6,6-trifluoro-5-(trimethylsilyl)oxy-1-methyl-5-(trifluoromethyl)-3Z-hexenyl)4H-inden-4-one in 4 ml of anhydrous tetrahydrofuran was added dropwise over a 10 min. period. The reaction mixture was then stirred at −78° C. for 2 hrs. It was then quenched with 10 ml of 2N Rochelle Salt, and warmed up to room temperature. After a further dilution with 30 ml 2N Rochelle Salt, it was extracted with 3×100 ml ethyl acetate. The combined organic layers were washed with brine, dried over sodium sulfate and evaporated to dryness to give 630 mg of crude intermediate. It was purified by FLASH chromatography with hexane-ethyl acetate (10:1), to give 220 mg of disilylated title compound. (The 25-silyl ether is hydrolyzed during this procedure).

To the solution of 220 mg of disilylated intermediate in 4 ml of anhydrous tetrahydrofuran was added 2.5 ml (2.5 mmole) of a 1M tetrabutylammonium fluoride in tetrahydrofuran under argon, and then stirred at room temperature for 18 hrs. At that time, 5 ml of water was added and stirred 15 min, followed by addition of 20 ml of brine and extraction with 3×90 ml of ethyl acetate. The combined organic layers were washed with water and brine, dried over sodium sulfate and evaporated to dryness. The crude product was purified by FLASH chromatography with hexane-ethyl acetate (2:1) to give 170 mg (53%) of the title compound as white foam.

EXAMPLE 33

1α-Fluoro-25-hydroxy-16-ene-23-yne-26,27-hexafluoro -20-epicholecalciferol

To a solution of 740 mg (1.57 mmole) of [3S-(1Z,3α, 5β)]-[2-[5-[[(1,1-dimethylethyl)dimethylsilyl]oxy]-3-fluoro-2-methylenecyclo-hexylidene]ethyl] diphenylphosphine oxide in 8 ml of anhydrous tetrahydrofuran at −78° C. was added with stirring 0.98 ml (1.57 mmole) of 1.6 M n-butyllithium in hexane, dropwise under argon. After stirring for five minutes, to thus formed red solution was added a solution of 262 mg (0.685 mmole) of [3aR-[1(S*),3aα,7aβ]]-3,3a,5,6,7,7a-hexahydro-7a-methyl-1-[6,6,6-trifluoro-5-hydroxy-1-methyl-5-(trifluoromethyl)-3-hexynyl]-4H-inden-4-one in 5 ml tetrahydrofuran, dropwise over a 10 min. period. The reaction mixture was then stirred at −78° C. for 2 hrs. It was then quenched by addition of 15 ml of a 1:1 mixture of 2N Rochelle salt and 2N potassium bicarbonate, followed by warming to room temperature. After 30 ml of the same salts mixture was added, it was extracted 3×100 ml of ethyl acetate. The combined organic layers were washed three times with water and brine, dried over sodium sulfate and evaporated to dryness. The residue was purified by FLASH chromatography on a 40 mm×6.5" silica gel column with hexane-ethyl acetate (5:1) to give 250 mg of the monosilylated title compound.

To the solution of 250 ml silyl intermediate in 3 ml of anhydrous tetrahydrofuran was added 2.8 ml (2.8 mmole) of 1M tetrabutyl-ammonium fluoride in tetrahydrofuran under argon. The reaction mixture was stirred at room temperature for 18 hrs. 10 ml of water was added and stirred for 15 min, then diluted with 20 ml brine and extracted with 3×90 ml ethylacetate. The organic layers were washed four times with water and brine, dried over sodium sulfate and evaporated to dryness. The crude product was purified by FLASH chromatography on a 30 mm×6" silica gel column with hexane-ethyl acetate (2:1) and by HPLC on a YMC 50 mm×50 cm silica column. It gave 175 mg (49%) of amorphous title compound.

EXAMPLE 34

1α-Fluoro-25-hydroxy-16,23E-diene-26,27-hexafluoro-20-epi-cholecalciferol

To a stirred solution of 350 mg (0.744 mmole) of [3S-(1Z,3α,5β)]-[2-[5-[[(1,1-dimethylethyl)dimethylsilyl]oxy]-3-fluoro-2-methylene-cyclohexylidene]-ethyl] diphenylphosphine oxide in 5 ml of anhydrous tetrahydrofuran at −78° C. was added 0.463 ml (0.74 mmole) of 1.6 M n-butyl lithium in hexane dropwise under argon. After stirring for 5 min, to thus formed red solution was added 230 mg (0.503 mmole) of [3aR-[1(S*,3E),3aα,7aβ]]-3,3a,5,6,7,7a-hexahydro-7a-methyl-1-[6,6,6-trifluoro-1-methyl-5-(trifluoro-methyl)-5-[(trimethylsilyl)oxy]-3-hexenyl]-4H-inden-4-one in 4.5 ml of anhydrous tetrahydrofuran dropwise over a 10 min period. The reaction mixture was stirred at −78° C. for two hours. It was then quenched by addition of 10 ml of a 1:1 mixture of 2N Rochelle salt and 2N potassium bicarbonate and warmed up to room temperature. After addition of 30 ml of the same salt mixture, it was extracted with 3×100 ml of ethyl acetate. The combined organic layers were washed three times with water and brine, dried over sodium sulfate and evaporated to dryness. The residue was purified by FLASH chromatography on a 40 mm×6" silica gel column with hexane-ethyl acetate to give 236 mg of disilylated title compound.

To the solution of 236 mg disilyl intermediate in 3.5 ml anhydrous tetrahydrofuran was added 3 ml (3 mmole) of a 1M tetrabutyl-ammonium fluoride in tetrahydrofuran under argon and the reaction mixture was stirred at room temperature for 18 hrs. Quenching was done by addition of 5 ml of water and stirring for 10 min. After dilution with 20 ml of brine, the mixture was extracted with 3×90 ml of ethyl acetate. The combined organic layers were washed with water and brine, dried over sodium sulfate and evaporated to dryness. The crude product was purified by FLASH chromatography on a 30 mm×6" silica gel column with hexane-ethyl acetate (2:1), and HPLC on a YMC 50 mm×50 cm silica column, to give 140 mg (53%) of amorphous title compound.

EXAMPLE 35

1,25-Dihydroxy-16-ene-23-yne-26,27-bishomo-20-epi-chole-calciferol

To a stirred solution of 435 mg (0.746 mmole) of [3S-(1Z,3α,5β)]-[2-[3,5-bis[[(1,1-dimethylethyl)dimethylsilyl]oxy]-2-methylenecyclo-hexylidene]ethyl] diphenylphosphine oxide in 5 ml of anhydrous tetrahydrofuran at −78° C. was added 0.465 ml (0.744 mmole) of 1.6 M n-butyllithium in hexane dropwise under argon. After stirring for 5 min, to thus obtained red solution was added a solution of 169 mg (0.451 mmole) of [3aR-[1(S*),3aα,7aβ]]-1-[5-ethyl-1-methyl-5-[(trimethyl-silyl)oxy]-3-heptynyl]-3,3a,5,6,7,7a-hexahydro-7a-methyl-4H-inden-4-one in 4 ml of anhydrous tetrahydro-furan, dropwise over a 10 min period. The reaction mixture was stirred at −78° C. for 2.5 hrs. It was then quenched by addition of 10 ml of a 1:1 mixture of 2N Rochelle salt and 2N potassium bicarbonate and warmed up to room temperature. After 25 ml of the same salt mixture was added, it was extracted with 3×90 ml of ethyl acetate. The combined organic layers were washed three times with water and brine, dried over sodium sulfate and evaporated to dryness. The residue was purified by FLASH chromatography on a 40 mm×6" silica gel column with hexane-ethyl acetate (40:1) to give 260 mg of trisilylated title compound.

To the solution of 260 mg trisilylated intermediate in 3 ml of anhydrous tetrahydrofuran was added 3 ml (3 mmole) of 1M tetrabutylammonium fluoride in tetrahydrofuran in argon atmosphere. The reaction mixture was stirred at room temperature for 17 hrs, and then quenched by addition of 10 ml water and stirring for 10 min. After dilution with 20 ml water and brine, it was extracted with 3×80 ml of ethyl acetate. The combined organic layers were washed four times with water and brine, dried over sodium sulfate and evaporated to dryness. The crude product was purified by FLASH chromatography on a 30 mm×5" silica gel column with hexane-ethyl acetate (1:3), to give 158 mg (80%) of the title compound, which was crystallized from methyl formate, m.p. 103–105° C.

EXAMPLE 36

1,25-Dihydroxy-16-ene-23-yne-26,27-bishomo-19-nor-20-epi-cholecalciferol

To a stirred solution of 300 mg (0.525 mmole) of [3R-trans-[2-[3,5-bis[[(1,1-dimethylethyl)dimethylsilyl]oxy] cyclohexylidene]ethyl]-diphenylphosphine oxide in 4 ml of anhydrous tetrahydrofuran at −78° C. was added 0.325 ml (0.520 mmole) of 1.6 M n-butyllithium in hexane, dropwise under argon. After stirring for 5 min, to thus obtained red solution was added a solution of 77 mg (0.205 mmole) of [3aR-[1(S*),3aα,7aβ]]-1-[5-ethyl-1-methyl-5-[(trimethyl-silyl)oxy]-3-heptynyl]-3,3a,5,6,7,7a-hexahydro-7a-methyl-4H-inden-4-one in 2.5 ml of anhydrous tetrahydrofuran, dropwise over a 5 min period. The reaction was stirred at −78° C. for 2.5 hrs. and then quenched by addition of 10 ml of a 1:1 mixture of 2N Rochelle salt and 2N potassium bicarbonate and warming up to room temperature. After a further dilution with 25 ml of the same salts mixture, it was extracted with 3×75 ml of ethyl acetate. The combined organic layers were washed three times with water and brine, dried over sodium sulfate and evaporated to dryness. The residue was purified by FLASH chromatography on a 30 mm×6.5" silica gel column with hexane-ethyl acetate to give 58 mg of trisilylated title compound.

To a solution of 124 mg of trisilyl intermediate (obtained from two preceding coupling reactions) in 2.5 ml of anhydrous tetrahydrofuran was added 2.5 ml (2.5 mmole) of 1M tetrabutylammonium fluoride in tetrahydrofuran under argon. The reaction mixture was stirred at room temperature for 40 hrs. It was then quenched by addition of 10 ml of water and stirring for 15 min. After dilution with 20 ml of water and brine, it was extracted with 3×70 ml of ethyl acetate. The combined organic layers were washed four times with water and brine, dried over sodium sulfate and evaporated to dryness. The crude product was purified by FLASH chromatography on a 30 mm×5" silica gel column with hexane-ethyl acetate (1:7), to give 74 mg (25.3%) of the title compound, which was recrystallized from methyl formate, m.p. 130–132° C.

EXAMPLE 37

1α-Fluoro-25-hydroxy-16-ene-23-yne-26,27-bishomo-20-epi-cholecalciferol

To a stirred solution of 390 mg (0.829 mmole) of [3S-(1Z,3α,5β)]-[2-[5-[[(1,1-dimethylethyl)dimethylsilyl]oxy]-3-fluoro-2-methylene-cyclohexylidene]ethyl] diphenylphosphine oxide in 5 ml of anhydrous tetrahydrofuran at −78° C. was added 0.53 ml (0.848 mmole) of 1.6 M n-butyllithium in hexane, dropwise under argon. After stirring for 5 min, to thus obtained red solution was added a solution of 200 mg (0.534 mmole) of [3aR-[1(S*),3aα,7aβ]]-1-[5-ethyl-1-methyl-5-[(trimethyl-silyl)oxy]-3-heptynyl]-3,3a,5,6,7,7a-hexahydro-7a-methyl-4H-inden-4-one in 4.5 ml of anhydrous tetrahydrofuran, dropwise over a 10 min period. The reaction mixture was then stirred at −78° C. for 2 hrs, and was quenched by addition of 10 ml of a 1:1 mixture of 2N Rochelle salt and 2N potassium bicarbonate and warming up to room temperature. After dilution with 30 ml of the same salts mixture, it was extracted with 3×100 ml ethyl acetate. The combined organic layers were washed three times with water and brine, dried over sodium sulfate and evaporated to dryness. The residue was purified by FLASH chromatography on 40 mm×6" silica gel column with hexane-ethyl acetate (30:1), to give 254 mg of disilylated title compound.

To a solution of 254 mg of disilyl intermediate in 3.5 ml anhydrous tetrahydrofuran was added under argon 3.5 ml (3.5 mmole) of 1M tetrabutylammonium fluoride in tetrahydrofuran. The reaction mixture was stirred at room temperature for 18 hrs, and then quenched by addition of 10 ml of water and stirring for 15 min. After dilution with 20 ml of water and brine, it was extracted with 3×80 ml of ethyl acetate. The combined organic layers were washed four times with water and brine, dried over sodium sulfate, and evaporated to dryness. The crude product was purified by FLASH chromatography on a 30 mm×6" silica gel column with hexane-ethyl acetate (7:4), and by HPLC on a YMC 50 mm×50 cm silica column with hexane-ethyl acetate (3:2), to give 159 mg (67.6%) of amorphous title compound.

EXAMPLE 38

1α-Fluoro-25-hydroxy-16-23E-diene-26,27-bishomo-20-epi-cholecalciferol

To a stirred solution of 240 mg (0.51 mmole) of [3S-(1Z,3α,5β)]-[2-[5-[[(1,1-dimethyl-ethyl)dimethylsilyl]oxy]-3-fluoro-2-methylene-cyclohexylidene]ethyl ]diphenyl-phosphine oxide in 5 ml of anhydrous tetrahydrofuran at −78° C. was added 0.319 ml (0.51 mmole) of 1.6 M n-butyllithium in hexane, dropwise under argon. After stirring for 5 min, to thus obtained red solution was added a solution of 103 mg (0.273 mmole) of [3aR-[1(S*,3E), 3aα, 7aβ]]-1-[5-ethyl-1-methyl-5-[(trimethylsilyl)oxy]-3-heptynyl]-3,3a,5,6,7,7a-hexahydro-7a-methyl-4H-inden-4-one in 4 ml of anhydrous tetrahydro-furan, dropwise over a 10 min period. The reaction mixture was stirred at −78° C. for 2 hrs, then placed in freezer (−20° C.) for one hour, quenched by addition of 10 ml of a 1:1 mixture of 2N Rochelle salt and 2N potassium bicarbonate and warmed up to room temperature. After dilution with additional 25 ml of the same salts mixture, it was extracted with 3×90 ml of ethyl acetate. The combined organic layers were washed three times with water and brine, dried over sodium sulfate and evaporated to dryness. The residue was purified by FLASH chromatography on a 30 mm×7" silica gel column with hexane-ethyl acetate (1:4), to give 145 mg of disilylated title compound.

To a solution of 145 mg of disilyl intermediate in 3 ml anhydrous tetrahydrofuran was added 1.7 ml (1.7 mmole) of 1M tetrabutyl-ammonium fluoride in tetrahydrofuran under argon. The reaction mixture was stirred at room temperature for 18 hrs, and then quenched by addition of 10 ml water and stirring for 15 min. It was diluted with 20 ml of water and brine and extracted with 3×80 ml ethyl acetate. The organic layers were washed four times with water and brine, dried over sodium sulfate, and evaporated to dryness. The crude product was purified by FLASH chromatography on a 30 mm×5" silica gel column with hexane-ethyl acetate (3:2), and by HPLC on a YMC 50 mm×50 cm silica gel column with hexane-ethyl acetate (1:1). It gave 90 mg (74%) of the title compound; m.p. 91–92° C., crystallization from methyl acetatehexane.

What is claimed is:

1. A compound of the formula

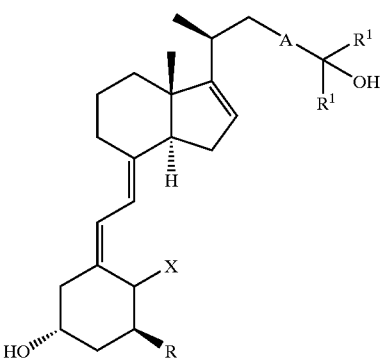

wherein R is hydrogen or hydroxy, each $R^1$ is ethyl, propyl, butyl, isopropyl or t-butyl, X is =$CH_2$, or when R is hydroxy, X is hydrogen or =$CH_2$, and A is —C≡C—,

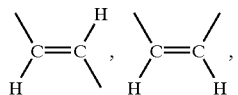

or
—$CH_2$—$CH_2$—.

2. A compound of claim 1, wherein R is hydroxy.
3. A compound of claim 2, wherein A is —C≡C—.
4. A compound of claim 2, wherein A is —$CH_2$—$CH_2$.
5. A compound of claim 2, wherein A is 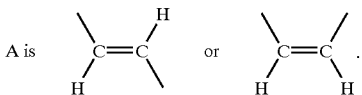

6. A compound of claim 2, wherein X is hydrogen.
7. A compound of claim 1, wherein R is hydrogen.
8. The compound of claim 1, 1,25-dihydroxy-16-ene-23-yne-26,27-bishomo-20-epi-cholecalciferol.
9. The compound of claim 1, 1,25-dihydroxy-16-ene-23-yne-26,27-bishomo-19-nor-20-epi-cholecalciferol.

* * * * *